(12) United States Patent
Chaudhary et al.

(10) Patent No.: US 10,557,805 B2
(45) Date of Patent: Feb. 11, 2020

(54) HIGH THROUGHPUT METHODS OF ANALYZING SEED COTTON USING X-RAY IMAGING

(71) Applicant: Monsanto Technology LLC, St. Louis, MO (US)

(72) Inventors: Govind Chaudhary, St. Louis, MO (US); Anju Gupta, St. Louis, MO (US); Kolbyn S. Joy, St. Louis, MO (US); John J. Kotyk, St. Louis, MO (US); Randall K. Rader, St. Louis, MO (US); Richard H. Sheetz, St. Louis, MO (US); Brad D. White, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 293 days.

(21) Appl. No.: 15/511,875

(22) PCT Filed: Sep. 25, 2015

(86) PCT No.: PCT/US2015/052133
§ 371 (c)(1),
(2) Date: Mar. 16, 2017

(87) PCT Pub. No.: WO2016/049408
PCT Pub. Date: Mar. 31, 2016

(65) Prior Publication Data
US 2018/0217072 A1    Aug. 2, 2018

Related U.S. Application Data

(60) Provisional application No. 62/055,861, filed on Sep. 26, 2014.

(51) Int. Cl.
*G01N 23/04* (2018.01)
*G01N 23/00* (2006.01)
(Continued)

(52) U.S. Cl.
CPC ....... *G01N 23/046* (2013.01); *G01N 33/0098* (2013.01); *G01N 23/10* (2013.01);
(Continued)

(58) Field of Classification Search
CPC ....... G01N 33/0098; G01N 2223/3307; G01N 2223/401; G01N 2223/643; G01N 23/046;
(Continued)

(56) References Cited

U.S. PATENT DOCUMENTS

| 4,041,315 A | 8/1977 | Hounsfield |
| 6,111,930 A | 8/2000 | Schipper |

(Continued)

OTHER PUBLICATIONS

International Search Report from corresponding PCT/US2015/052133 dated Dec. 18, 2015.

*Primary Examiner* — Irakli Kiknadze
(74) *Attorney, Agent, or Firm* — Sandberg Phoenix & von Gontard PC

(57) ABSTRACT

A system for analyzing intact cotton, wherein the system comprises an X-ray scanner system and a plurality of sample containers, wherein at least one seed cotton sample container is structured and operable to retain a respective one of a plurality of intact cotton samples. The system additionally comprises a sample support platform that is structured and operable to move the plurality of sample containers past an image data generation assembly of the X-ray scanner system. The system further comprises a computer based system that is structured and operable to execute image analysis software to determine at least one metric of at least one of the intact cotton samples.

13 Claims, 24 Drawing Sheets

(51) Int. Cl.
*G01N 23/046* (2018.01)
*G01N 33/00* (2006.01)
*G01N 23/10* (2018.01)

(52) U.S. Cl.
CPC ............... *G01N 2223/3307* (2013.01); *G01N 2223/401* (2013.01); *G01N 2223/643* (2013.01)

(58) Field of Classification Search
CPC ............ G01N 23/10; G01N 2223/419; G01N 33/362; G01N 2223/301; G01N 23/20; G01N 23/20025; G01N 23/20016; G01N 2035/0443; G01N 2223/076; G01N 23/207; G01N 23/2204; G01N 23/223; G01N 35/025; G01N 35/04; G01N 2035/00356; G01N 2035/0408; G01N 2035/0427; G01N 2035/0465; G01N 2035/0472
USPC .......................................... 378/4, 19, 57, 58
See application file for complete search history.

(56) References Cited

U.S. PATENT DOCUMENTS

| | | |
|---|---|---|
| 2003/0123608 A1 | 7/2003 | Sari-Sarraf et al. |
| 2006/0042528 A1 | 3/2006 | Deppermann |
| 2010/0150308 A1 | 6/2010 | Tsuno et al. |
| 2011/0019796 A1 | 1/2011 | Wuestenbecker et al. |
| 2011/0026670 A1 | 2/2011 | Lin et al. |
| 2013/0057871 A1 | 3/2013 | Kim et al. |

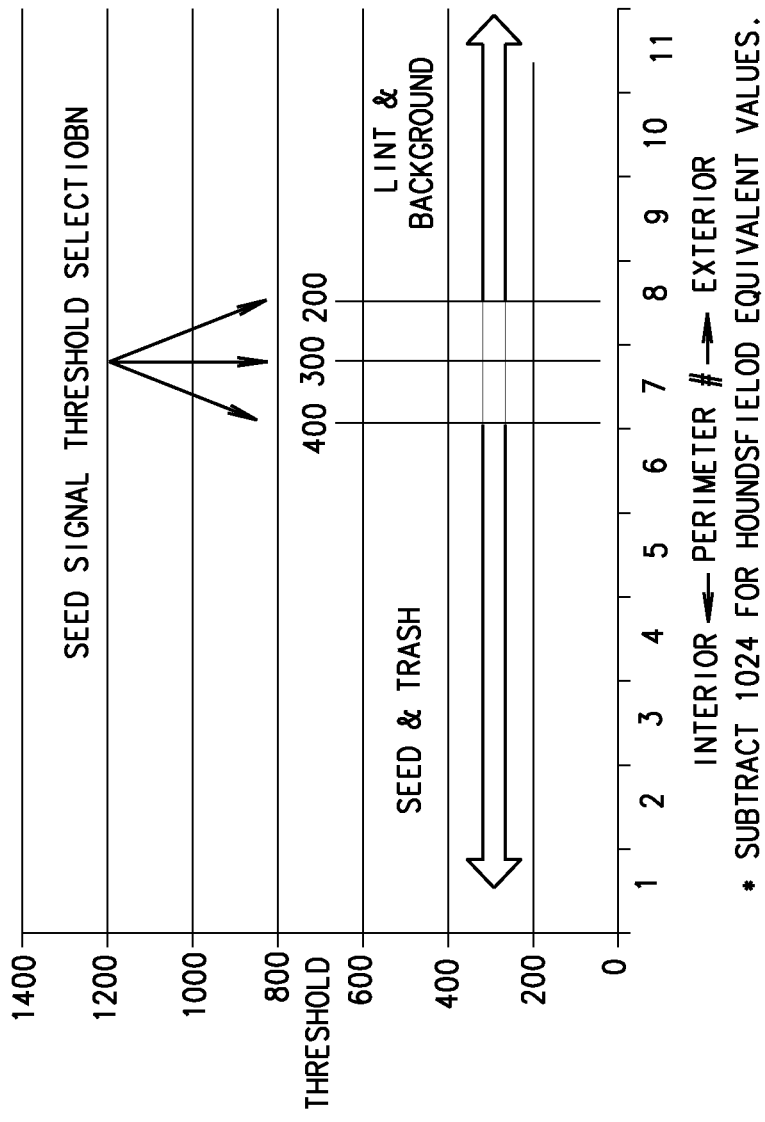
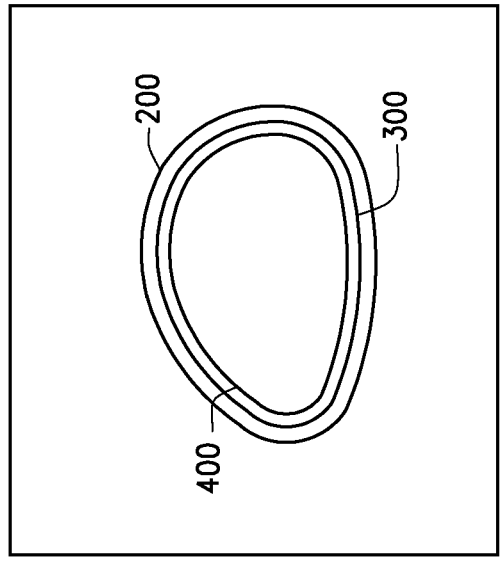
FIG. 9D

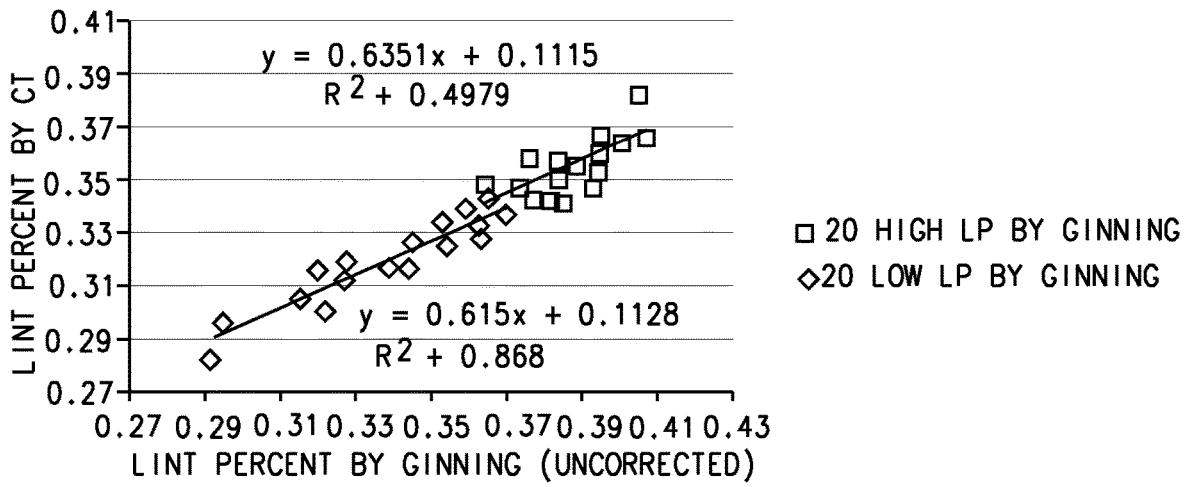
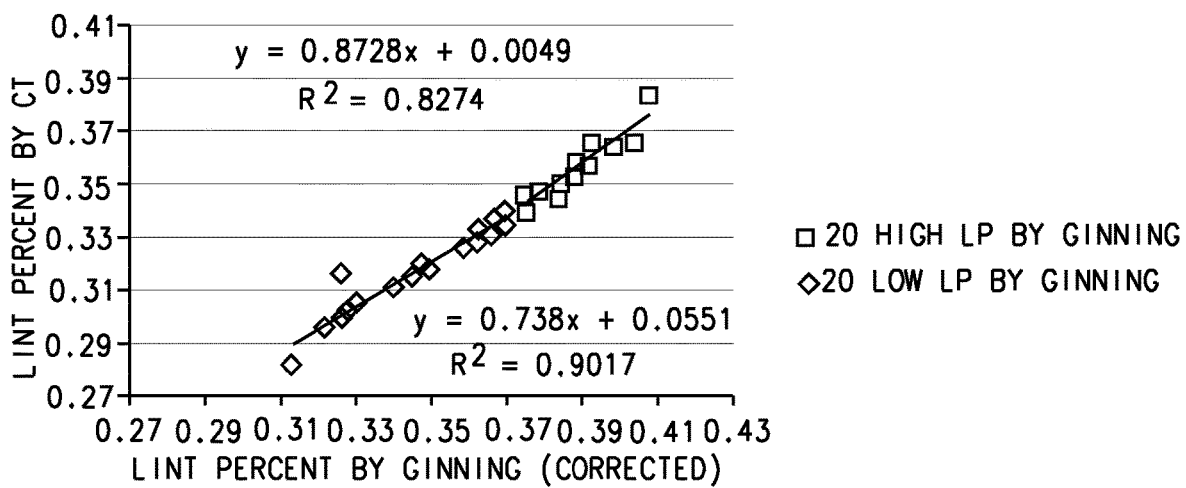
FIG. 16

COMPARISON OF METHODS OF DEETERMINING SEED METRICS

| METHOD | DENSITY | VOLUME ON A BULK SEED BASIS | VOLUME ON AN INDIVIDUAL SEED BASIS | SEED SURFACE AREA ON AN INDIVIDUAL SEED BASIS | THROUGHPUT |
|---|---|---|---|---|---|
| SEED INDEX (WT OF 100 FUZZY SEEDS) | N, CONFOUNDED WITH VOLUME | N, CONFOUNDED WITH DENSITY | N | N | LOW |
| ETOH DISPLACEMENT | N | Y | Y | N | VERY LOW FOR BULK, EXTREMELY LOW FOR INDIVIDUAL SEED |
| AIR DISPLACEMENT (PYCHNOMETER) | N | Y | Y | N | EXTREMELY LOW |
| WinSEEDLE (2-D IMAGE ANALYSIS | N | Y | Y | Y | MODERATE |
| CT SCAN (3-D IMAGE ANALYSIS | Y | Y | Y | Y | VERY HIGH |

FIG. 17

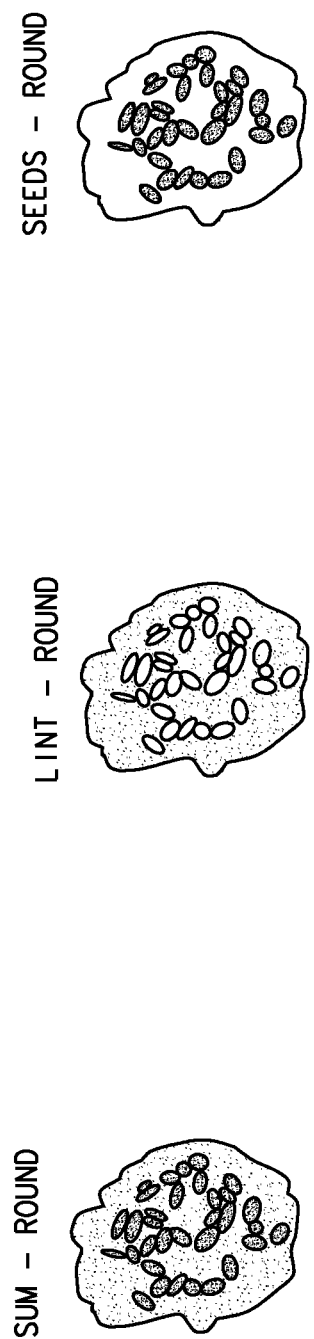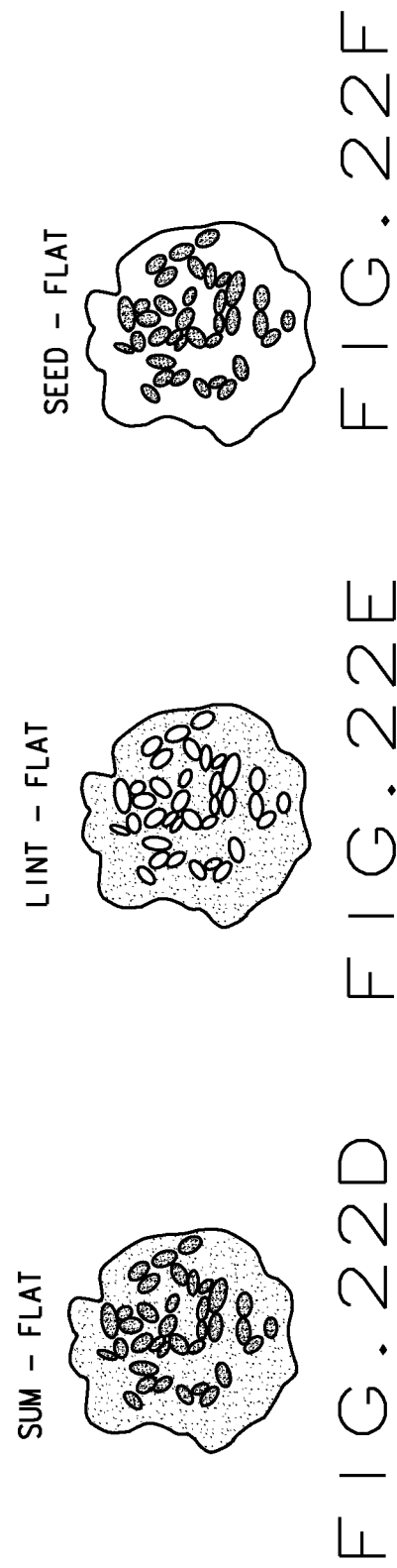

HIGH THROUGHPUT METHODS OF ANALYZING SEED COTTON USING X-RAY IMAGING

CROSS-REFERENCE TO RELATED APPLICATIONS

The present invention is the US national stage under 35 U.S.C. § 371 of International Application No. PCT/US2015/052133, which was filed on Sep. 25, 2015, and which claims the benefit of U.S. Provisional Application No. 62/055,861, filed on Sep. 26, 2014. The disclosure of the above application is incorporated herein by reference in its entirety.

FIELD

The present teachings relate to systems and methods for analyzing seed cotton, and more particularly to systems and methods for analyzing seed cotton using X-ray systems.

BACKGROUND

The statements in this section merely provide background information related to the present disclosure and may not constitute prior art.

The majority of the value of a cotton crop is in the cotton lint. Therefore, the determination of the projected lint yield for a cotton crop grown using a particular seed or seed type is very beneficial to seed breeders and ultimately the cotton farmers.

Typically, to determine projected lint yield for various types of cotton seeds (e.g. different varieties), seed breeders grow test plots using the various different types of seed. Subsamples of cotton from each test plot are then harvested, weighed and the lint is separated from the seed. The resulting lint is then weighed and a percentage of lint relative to the amount of seed cotton in each subsample is calculated and used to determine the lint yield for each subsample and hence, for each seed type. Typically, the lint is separated from the seed using a mechanical means such as a cotton gin.

Furthermore, researchers desiring to improve the cotton crop also commonly gather information about the seeds themselves. To collect data about seed quality characteristics like seed size, volume, shape, mass, germination potential, and/or the presence and/or extent of disease and/or damage, present methods require that samples of seed cotton are ginned first to remove the surrounding lint so that the seeds can be adequately analyzed.

Ginning cotton is a laborious, time and cost intensive process, it poses various safety hazards, and the amount of lint yielded can vary from cotton gin to cotton gin and from operator to operator due to sample loss and procedural inconsistencies.

SUMMARY

The present disclosure provides systems and methods for determining lint percent and various other metrics of seed cotton. Generally, the systems and methods disclosed here utilize an X-ray scanner system to scan a plurality of seed cotton samples at a high throughput rate. Then proprietary image analysis software, i.e., image analysis program(s) and/or algorithm(s), is used to determine lint percent and various other metrics of the seed cotton samples and the results can be used to improve breeding decisions related to the population from which the sample was taken. The presently disclosed systems and methods increase the accuracy and precision of lint yield and quality measurements, and reduce the cost, labor, hazards and inconsistencies that occur when lint percent is determined by physically separating the lint from the seed.

Other advantages of the systems and methods disclosed herein are that such systems and methods can additionally be employed to detect and score various other metrics, i.e., physical and/or genetic traits, of the cotton seed and/or the lint that are difficult to determine using known systems and methods. For example, the systems and methods disclosed herein can be employed to determine important seed quality characteristics, such as: the proportion of cotton seeds that have a "not-filled" or substantially "hollow" phenotype (i.e., seed X-ray attenuation that relates to seed maturity); seed maturity; the number of lint fibers per unit sample; lint density; oil content of the seed; seed size; seed shape; seed surface area; seed viability; seed count; seed volume; seed damage (e.g. resulting from mechanized harvesting and/or post-harvest processing); the presence and/or extend of seed disease, determination of the amount of trash (e.g., plant stems) and many other characteristics useful for breeding improved cotton varieties. These and other embodiments can be used to gather information about cotton seeds, regardless of whether the seeds are separated from the lint.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 9D is an exemplarily illustration demonstrating how the accuracy of the image analysis software is dependent upon the selected attenuation threshold value utilized during image analysis, in accordance with various embodiments of the present disclosure.

FIG. 16 is a graph illustrating the LP determined after the samples had been ginned (as shown in FIG. 10) before and after application of the correction factor and the LP determined by computed tomography of intact cotton samples, in accordance with various embodiments of the present disclosure.

FIG. 17 provides a comparison and contrast of different methods for determining seed metrics, in accordance with various embodiments of the present disclosure.

Figure 18:
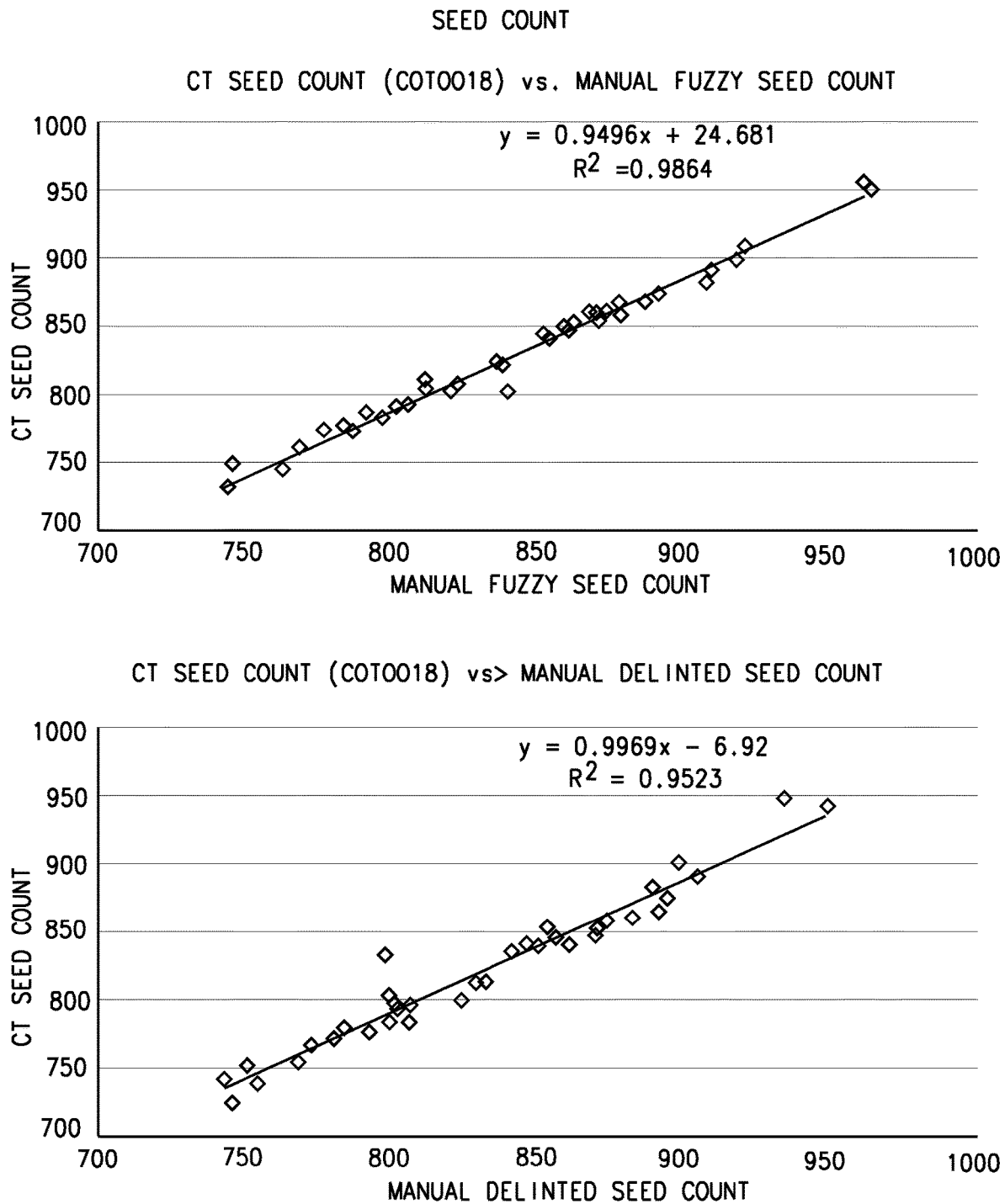

FIG. 18 is a graphical illustration showing the number of seeds determined to be in each of the 40 samples utilizing the system 10 versus a manual count of seeds from each respective sample after the samples had been ginned, and versus a manual count of seeds from each respective sample after the seeds had been delinted, in accordance with various embodiments of the present disclosure.

Figure 19:
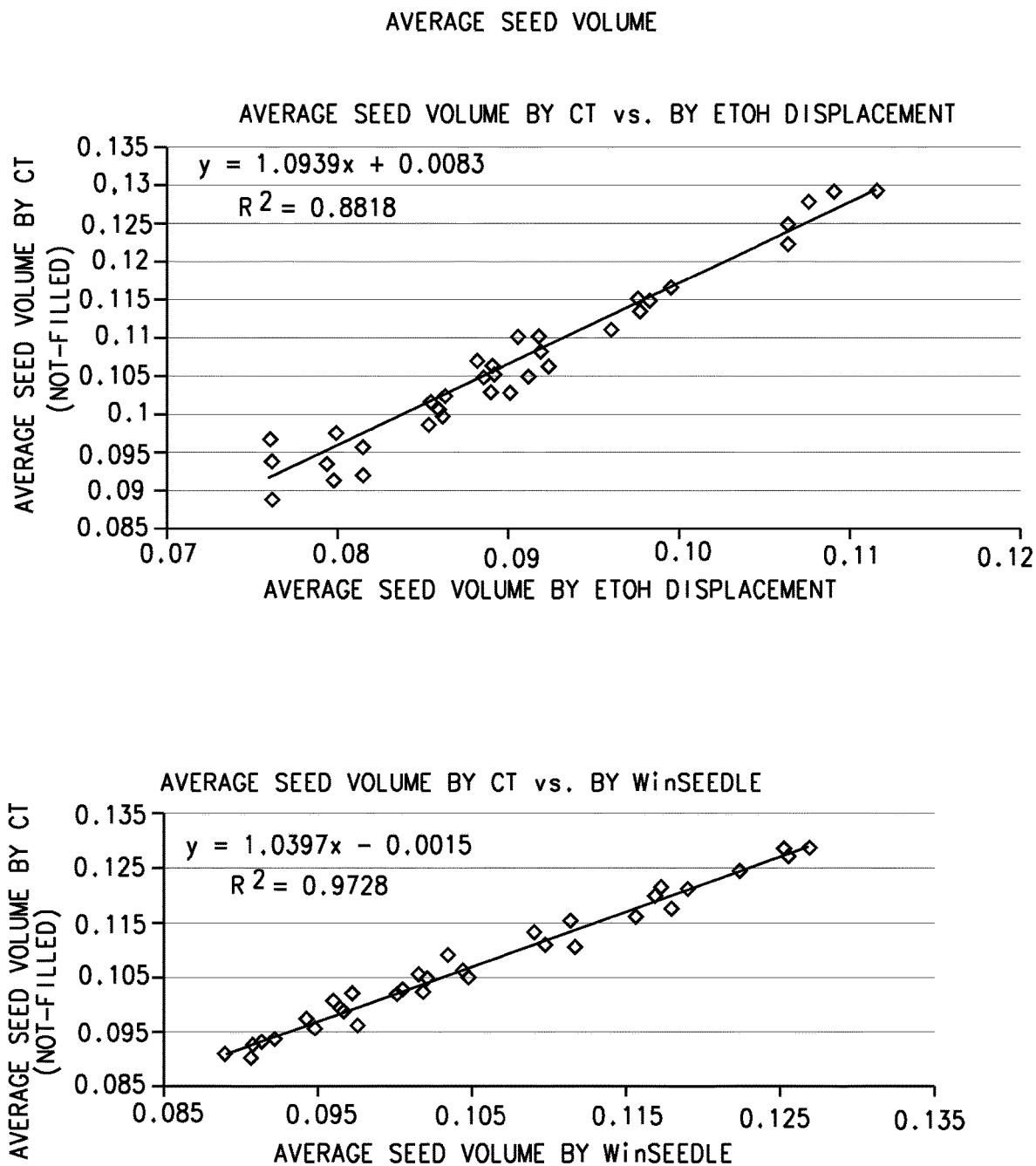

FIG. 19 provides graphical illustrations of average seed volume by computed tomography versus ETOH displacement and versus the average seed volume determined by WinSEEDLE™, in accordance with various embodiments of the present disclosure.

Figure 20:
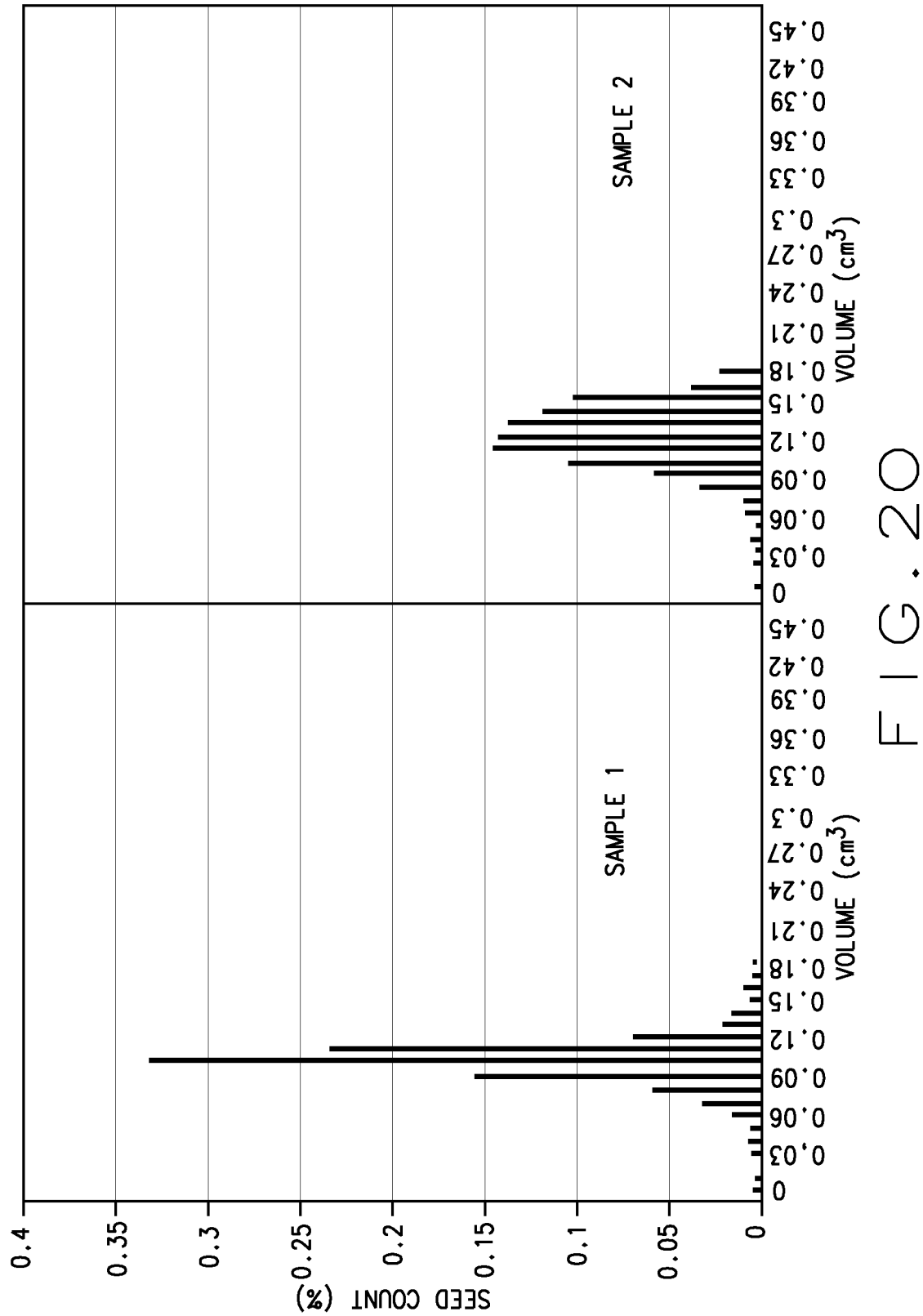

FIG. 20 provides a histogram of seed volume, as determined by the computed tomography methods described herein, verses the total number of seeds for two independent samples of seed cotton, in accordance with various embodiments of the present disclosure.

Figure 21:
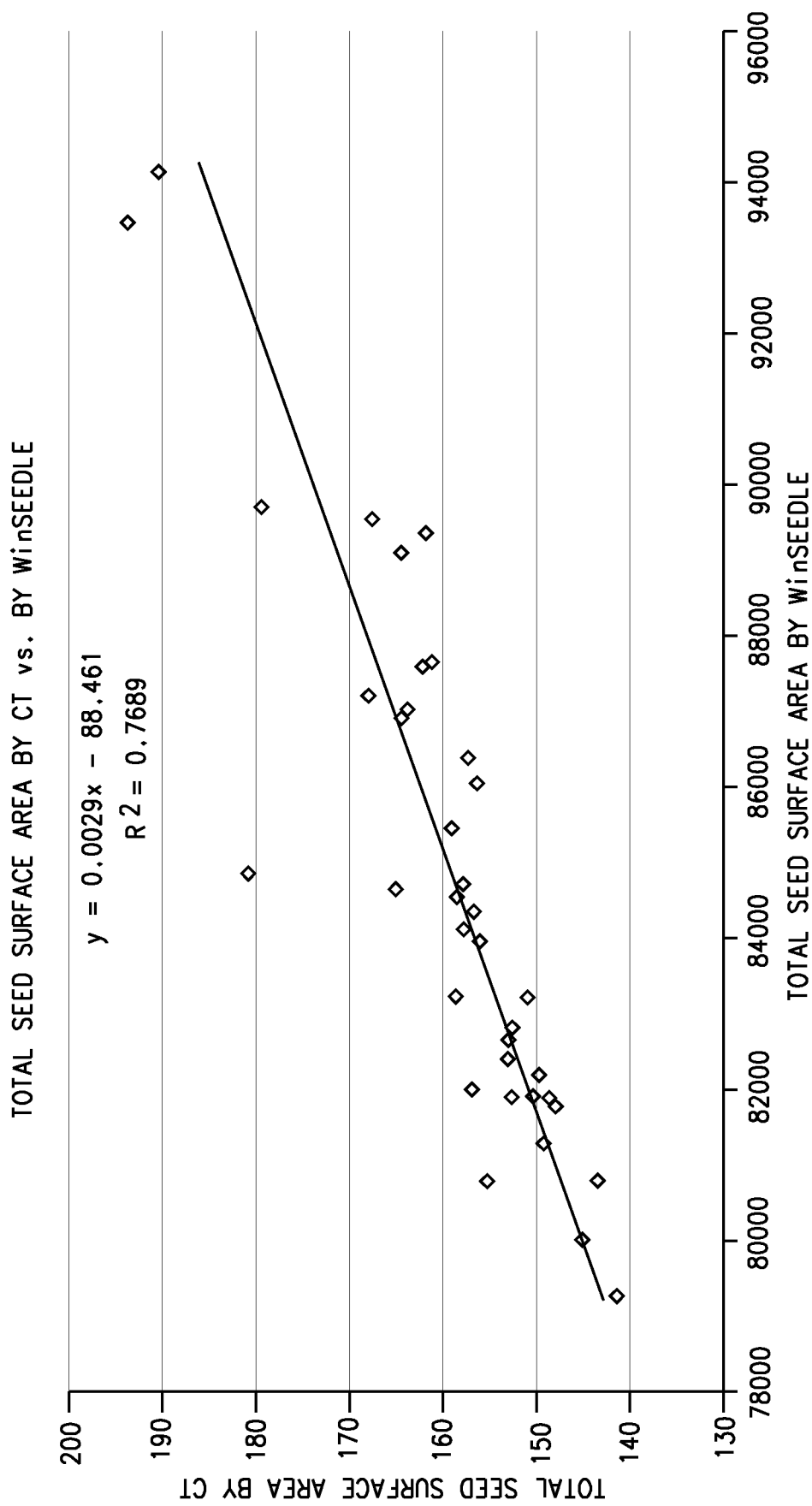

FIG. 21 is a graph illustrating the total seed surface area by computed tomography (not filled) versus total seed surface area by WinSEEDLE™, in accordance with various embodiments of the present disclosure.

Figure 1:
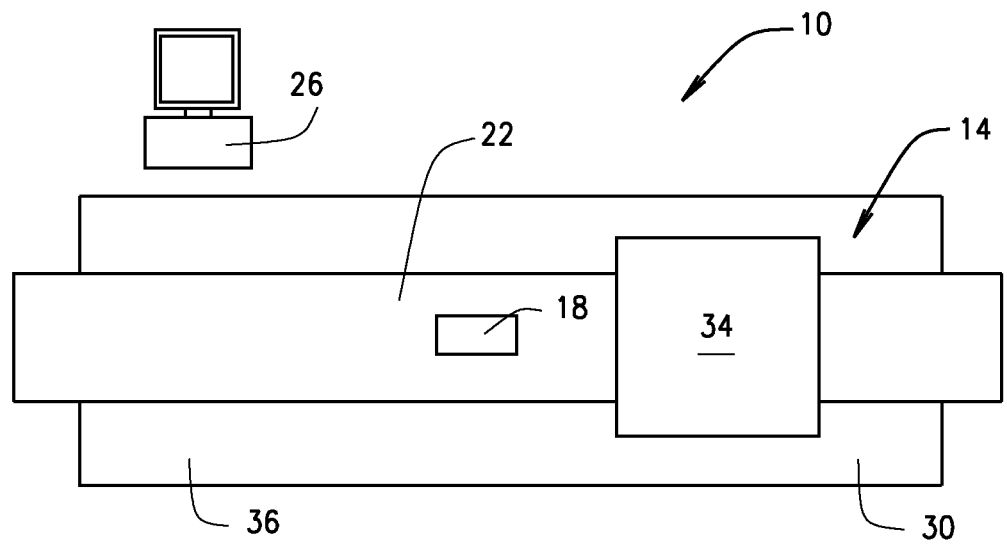
FIG. 1 is a block drawing exemplarily illustrating a seed cotton analysis system for determining lint percent and other seed cotton metrics, in accordance with various embodiments of the present disclosure.
Figure 1A:
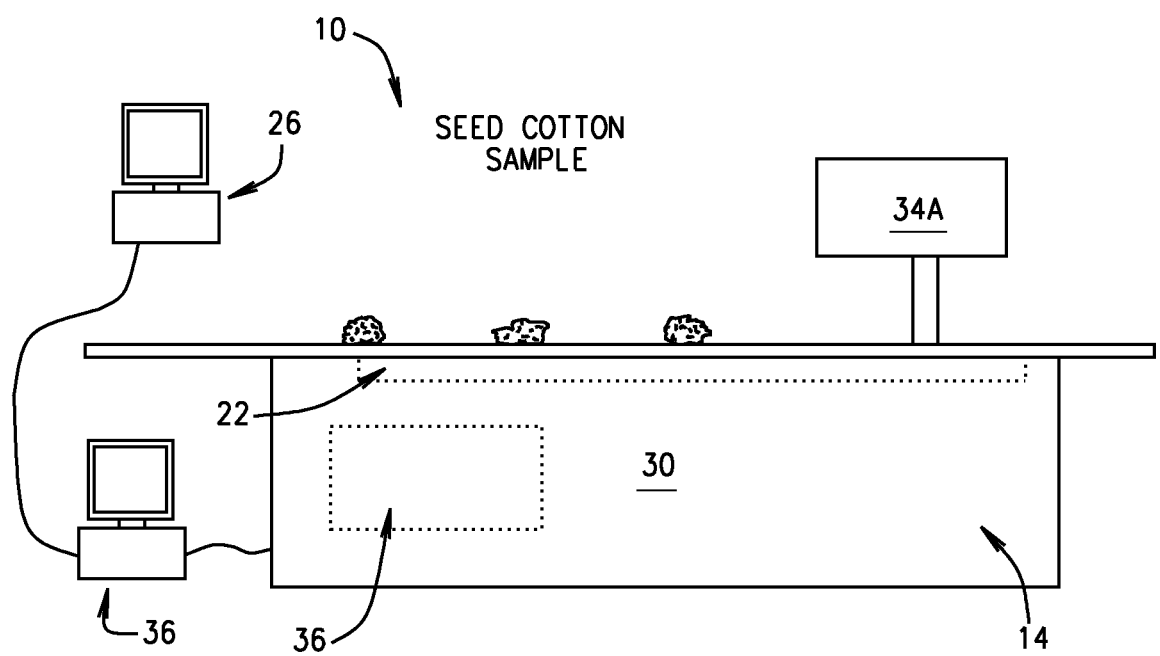
FIG. 1A is a schematic of the seed cotton analysis system shown in FIG. 1 comprising a two-dimensional (2D) image data generation system, in accordance with various embodiments of the present disclosure.

FIG. 22A is an exemplary illustration of a 2D X-ray image data of a 'round' seed cotton sample using the 2D X-ray image data generation assembly of the system 10 shown at least in FIGS. 1 and 1A, in accordance with various embodiments of the present disclosure.

FIG. 22B is an exemplary illustration of the X-ray image data shown in FIG. 22A after processing by the image analysis software, showing the amount of lint in the section of seed cotton shown in FIG. 22A, in accordance with various embodiments of the present disclosure.

FIG. 22C is an exemplary illustration of the 2D X-ray image data shown in FIG. 22A after processing by image analysis software, showing the number, size and amount of seed in the section of seed cotton shown in FIG. 22A, in accordance with various embodiments of the present disclosure.

FIG. 22D is an exemplary illustration of a 2D X-ray image data of a 'flat' seed cotton sample using the 2D X-ray image data generation assembly of the system 10 shown at least in FIGS. 1 and 1A, in accordance with various embodiments of the present disclosure.

FIG. 22E is an exemplary illustration of the X-ray image data shown in FIG. 22D after processing by the image analysis software, showing the amount of lint in the section of seed cotton shown in FIG. 22D, in accordance with various embodiments of the present disclosure.

FIG. 22F is an exemplary illustration of the 2D X-ray image data shown in FIG. 22D after processing by image analysis software, showing the number, size and amount of seed in the section of seed cotton shown in FIG. 22D, in accordance with various embodiments of the present disclosure.

Corresponding reference numerals indicate corresponding parts throughout the several views of drawings.

DETAILED DESCRIPTION

The following description is merely exemplary in nature and is in no way intended to limit the present teachings, application, or uses. Throughout this specification, like reference numerals will be used to refer to like elements.

Referring to FIG. 1, in various embodiments, the present disclosure provides a seed cotton analysis system 10 that is structured and operable to analyze a plurality of intact cotton samples and determine at least one characteristic or metric of each of the intact cotton samples. As used herein, the term 'intact cotton' will be understood to mean cotton samples wherein the seeds remain intermixed with the lint and the term is used interchangeably herein with the terms 'seed cotton', 'unginned cotton' and 'preginned cotton', that is, cotton bolls where the lint and seed have not been separated and remain intact. Thus, as used herein, an intact seed cotton sample or an intact cotton sample is one wherein the lint fibers remain attached and/or have not been physically separated (e.g., by ginning or by hand) from the seeds from which they developed.

In various embodiments, an intact cotton sample is one that remains growing from its mother plant and the mother plant remains growing in a field, greenhouse, growth chamber, or other growing area. In various embodiments, the intact cotton sample is harvested from the growing area and yet remains attached to the stem or flower of the mother plant. In various embodiments, the cotton sample is harvested by removing it from the mother plant, e.g., hand picking or mechanical harvesting and yet remains attached to the stem or flower of the mother plant.

The system 10 can analyze each intact cotton sample to determine: the lint percent of each sample; the number of seeds in each sample; a seed density of each sample; the number of lint fibers in each sample; a lint density of each sample; the amount of trash (e.g., plant stems) in each sample, and other important characteristics related to cotton quality. The system 10 can also detect and quantify important characteristics related to seed quality of each seed in a sample of seed cotton, including a seed maturity metric; a seed viability metric; a seed oil content metric; a seed volume metric; a size, shape and/or surface area metric; a disease metric; a seed damage metric; etc. Embodiments described herein are useful for collecting these and other seed quality data, regardless of whether the seeds have been separated.

The system 10 generally comprises an X-ray scanner system 14, a sample delivery or support platform 22, and a computer based data analysis system 26. In various embodiments, the X-ray scanner system 14 can comprise a three-dimensional (3D) X-ray computed tomography (CT) scanner system, while, alternatively, in other embodiments, the X-ray scanner system 14 can comprise a two-dimensional X-ray system. The X-ray scanner system 14 generally includes a base cabinet 30 and an image data generation assembly 34 mounted to or otherwise disposed adjacent (e.g., above) the base cabinet 30. In various implementations, the base cabinet 30 has disposed therein, or has operationally connected thereto, various mechanical, electrical, electrical-mechanical assemblies and subsystems (not shown) and a computer based image generation subsystem 36 that are structured and operable to impart and control the operation of the X-ray scanner system 14 to capture image data and generate two-dimensional (2D) or three-dimensional (3D) images of one or more, e.g., a plurality of, the seed cotton samples. In various embodiments, the system 10 can include one or more sample containers 18 that are structured and operable to have disposed therein and retain a respective seed cotton sample. Each seed cotton sample comprises an amount of intact cotton grown from a particular type of seed, i.e., seed having particular genotype and/or phenotype characteristics or traits. Although it is envisioned that the system 10 can operate, as described herein, to analyze each respective sample without the samples being retained within a container 18, for clarity and simplicity, the structure and operation of the system 10 will be described herein with regard to embodiments wherein each seed cotton sample is deposited and retained within a respective container 18.

The X-ray scanner system 14, particularly the image data generation assembly 34, is structured and operable to emit a plurality of X-ray signals (referred to herein as an imaging field) and capture X-ray image data of the intact cotton samples disposed within the sample containers 18 after the sample containers are placed within or passed through the imaging field of the image data generation assembly 34, as described further below. Subsequently, the captured X-ray image data is manipulated or processed utilizing the image generation subsystem 36 and/or the computer based data analysis system 26 to generate images of specific areas of the intact cotton samples, e.g., seed cotton samples disposed within the sample containers 18. Particularly, digital geometry processing is executed by the image generation subsystem 36 and/or the computer based data analysis system 26 to convert the raw X-ray data, or synogram, into one or more 2D images or a stack of 3D images that cover the entire volume of the inside of the intact cotton samples. Thereafter, the 2D or 3D images can be analyzed via execution of image analysis software by the computer based data analysis system 26 to generate the desired seed cotton sample metrics.

Referring now to FIG. 1A, in various embodiments, the image data generation assembly 34 can comprise a 2D X-ray scanner system 34A. In such embodiments, the 2D X-ray scanner system 34A emits a plurality of X-ray signals, i.e., an imaging field, and the image generation subsystem 36, via the 2D X-ray scanner system 34A, captures image data of the respective intact cotton sample within the imaging field and generates 2D images of the sample. Subsequently, the image generation subsystem 36 and/or the computer based data analysis system 26 manipulate or process the captured X-ray image data and generate images of specific areas of the respective intact cotton sample. Particularly, as described above, digital geometry processing is executed by the image generation subsystem 36 and/or the computer based data analysis system 26 to convert the raw X-ray data into one or more 2D images that cover the entire volume of the inside of the intact cotton samples. Thereafter, the 2D images can be analyzed via execution of image analysis software by the computer based data analysis system 26 to generate the desired seed cotton sample metrics.

Figure 1B:
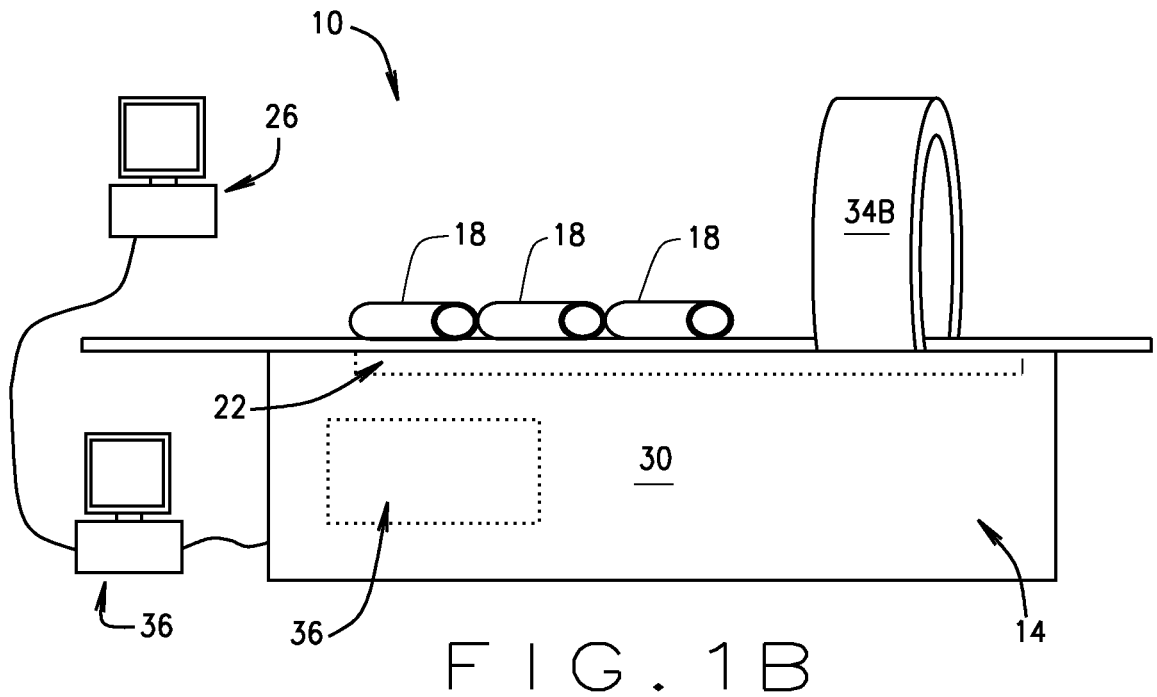
FIG. 1B is a schematic of the seed cotton analysis system shown in FIG. 1 comprising a three-dimensional (3D) image data generation system (e.g., a computed tomography (CT) system), in accordance with various embodiments of the present disclosure.

Referring now to FIG. 1B, in various embodiments, the image date generation assembly 34 can comprise a 3D X-ray scanner system 34B, e.g., a computed tomography (CT) scanner system. In such embodiments, the 3D X-ray scanner system 34B (often referred to herein as the CT scanner system) emits a plurality of X-ray signals, i.e., an imaging field, and the image generation subsystem 36, via the CT scanner system 34A, captures image data of the respective intact cotton sample within the imaging field and generates 3D images of the sample. Subsequently, the image generation subsystem 36 and/or the computer based data analysis system 26 manipulate or process the captured X-ray image data and generate tomographic images (i.e., virtual 'slices') of specific areas of the respective intact cotton sample. Particularly, as described above, digital geometry processing is executed by the image generation subsystem 36 and/or the computer based data analysis system 26 to convert the raw CT data, or synogram, into a stack of 2D images that cover the entire 3D volume of the inside of the intact cotton samples. Thereafter, the 3D images, i.e., 3D image data, can be analyzed via execution of image analysis software by the computer based data analysis system 26 to generate the desired seed cotton sample metrics.

Referring now to FIGS. 1, 1A and 1B, in various embodiments, the computer based data analysis system 26 of the seed cotton analysis system 10 is communicatively connected (wired or wirelessly) to the computer based image generation subsystem 36. Alternatively, the analysis system 26 can be separate from the image generation subsystem 36, i.e., not communicatively connected to the image generation subsystem 36, wherein data is physically transferred between the two via any suitable portable memory device. In yet other embodiments, the analysis system 26 of the seed cotton analysis system 10, and the image generation subsystem 36, can be same computer based device. That is, it is envisioned that the image analysis software can be stored on and executed by the image generation subsystem 36.

The sample delivery platform 22 can comprise any, conveyance system, mechanism, device, apparatus or means for supporting and/or providing and/or presenting the samples and/or sample containers 18 to the X-ray scanner system 14, such that the respective samples and/or sample containers 18 can be scanned by the X-ray scanner system 14, as described herein. For example, in various instances the sample delivery/support platform 22 can be any conveyance system, mechanism, device, apparatus structured and operable to convey the one of more of samples and/or sample containers 18 past or through the imaging field of the image data generation assembly 34 (e.g., 34A and 34B). In various other instances, the sample delivery/support platform 22 can be any stationary mechanism, device, apparatus, one which the samples and/or sample containers 18 can be placed within the imaging field, so that the X-ray scanner system 14 can capture (i.e., generate and collect) the image data of each seed cotton sample. In still other instances, the sample delivery/support platform 22 can comprise the field in which live plants are growing having unharvested/unpicked samples still on the plants, wherein the X-ray scanner system 14 can be a mobile device that is moved through the field to capture (i.e., generate and collect) the image data of each seed cotton sample.

Figure 2A:
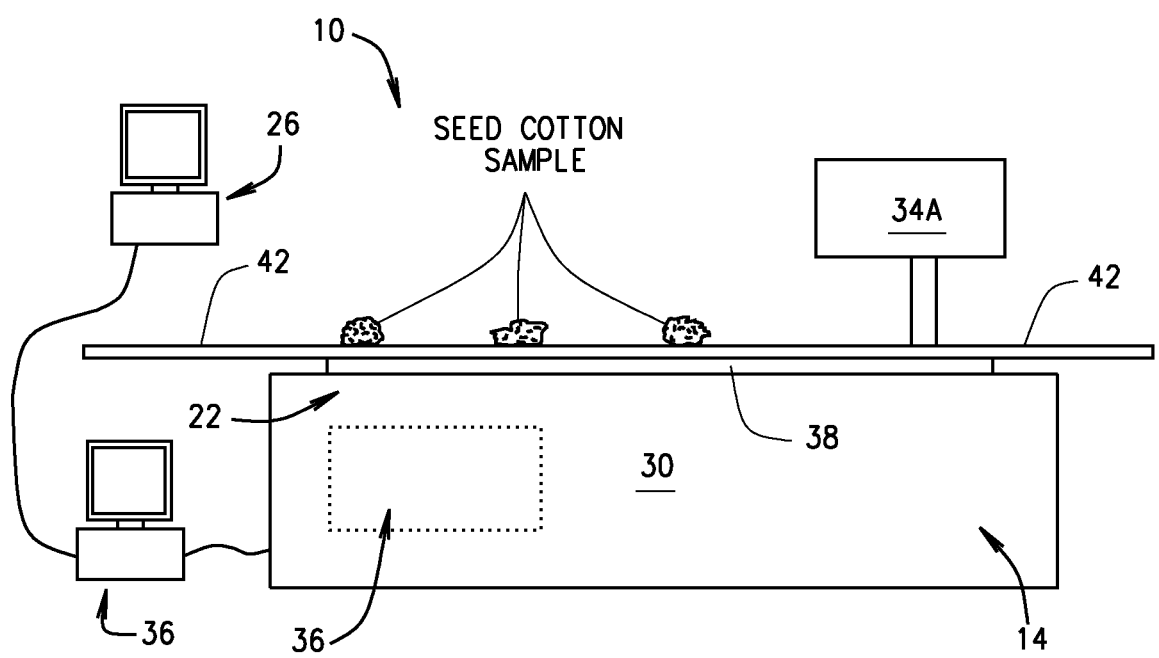
FIG. 2A is an isometric view of an X-ray computed tomography machine included in the system shown in FIG. 1 having a sample delivery or support platform comprising a linear stage, in accordance with various embodiments of the present disclosure.
Figure 2B:
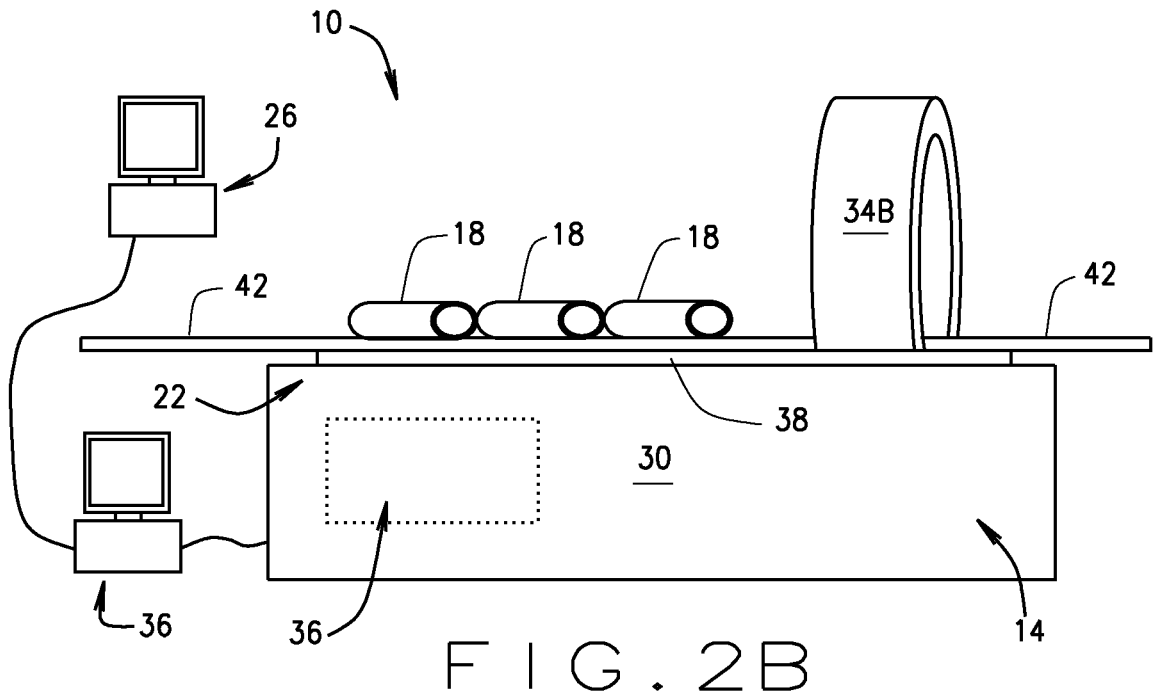
FIG. 2B is an isometric view of an X-ray computed tomography machine included in the system shown in FIG. 1 having the sample delivery or support platform comprising a linear stage, in accordance with various other embodiments of the present disclosure.

For example, as exemplarily illustrated in FIGS. 2A and 2B, in various embodiments, it is envisioned that the sample delivery/support platform 22 can comprise a linear stage 38 mounted to at least a portion of the base cabinet 30 of the X-ray scanner system 14 and a bed 42 mounted to the linear stage 38. The linear stage 38 is structured and operable to linearly move at least a portion of the bed 42 through the imaging field of the image data generation assembly 34 (e.g., 34A and 34B). More specifically, the sample(s), or sample container(s) 18 having the respective seed cotton sample disposed therein, can be placed on the bed 42. Subsequently, the linear stage 38 can be actuated to move the bed 42 along a linear axis of the linear stage 38, thereby positioning each seed cotton sample, or sample container 18 with respective seed cotton sample, within the imaging field for a predetermined amount of time, or conveying each sample or sample container 18 through the imaging field of the image data generation assembly 34 such that image data of each respective seed cotton sample can be captured.

Although it should be understood that the system 10 as described herein can be utilized on intact cotton samples that are not disposed within a sample container 18, and remain within the scope of the present disclosure. Throughout the present disclosure the system 10 may be exemplarily described and/or illustrated having each seed cotton sample disposed within a respective sample container 18.

Figure 3A:
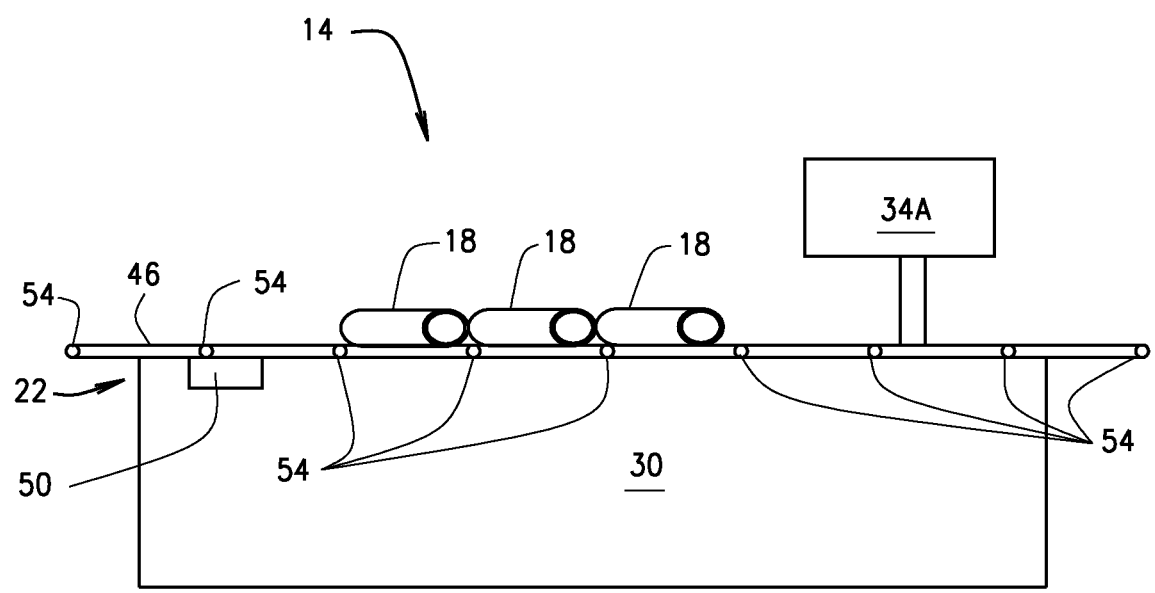
FIG. 3A is schematic of the X-ray computed tomography machine included in the system shown in FIG. 1 having the sample delivery or support platform comprising a conveyor belt assembly, in accordance with various embodiments of the present disclosure.
Figure 3B:
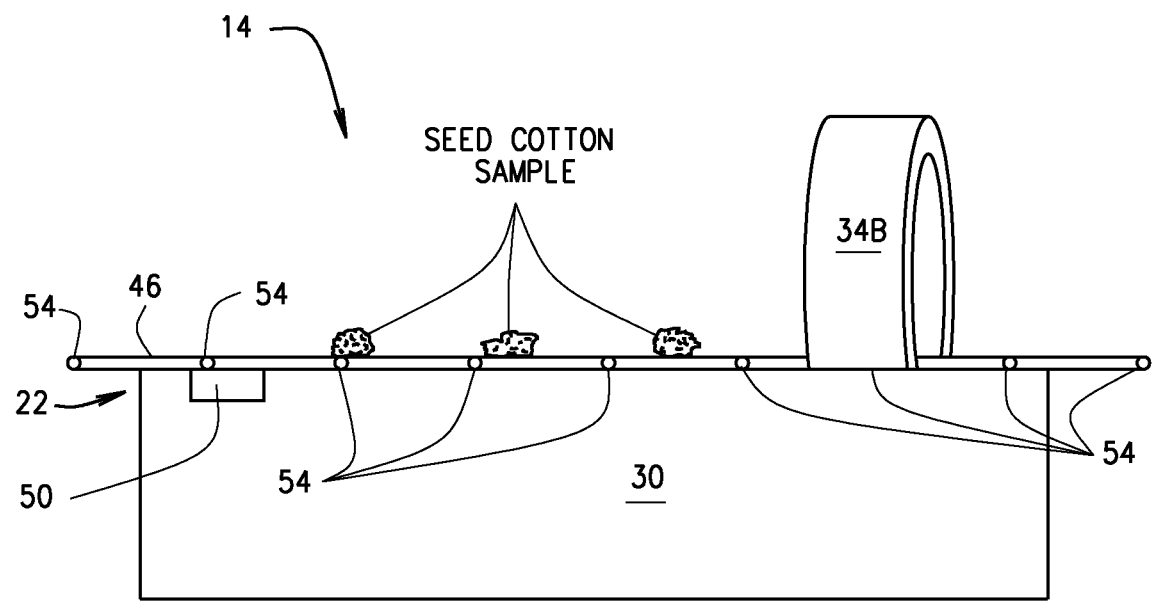
FIG. 3B is schematic of the X-ray computed tomography machine included in the system shown in FIG. 1 having the sample delivery or support platform comprising a conveyor belt assembly, in accordance with various other embodiments of the present disclosure.

Referring now to FIGS. 3A and 3B, in various other embodiments, it is envisioned that the sample delivery/support platform 22 can comprise a conveyor belt assembly rotatably mounted to the base cabinet 30 of the X-ray scanner system 14. The conveyor belt assembly generally comprises a continuous conveyor belt 46 rotatably driven by a belt motor 50. The motor 50 is operable to revolve the belt 46 over and around a plurality of bearing rollers 54. More specifically, the sample(s), or sample container(s) 18 having the respective seed cotton sample disposed therein, can be placed on the conveyor belt 46. Subsequently, the motor 50 can be actuated to revolve the belt 46 across or around the bearing rollers 54, thereby positioning each sample or sample container 18 within the imaging field for a predetermined amount of time, or conveying each seed cotton sample, or sample container 18 and respective seed cotton sample, through the imaging field of the image data generation assembly 34 such that image data of each respective seed cotton sample can be captured.

Figure 4A:
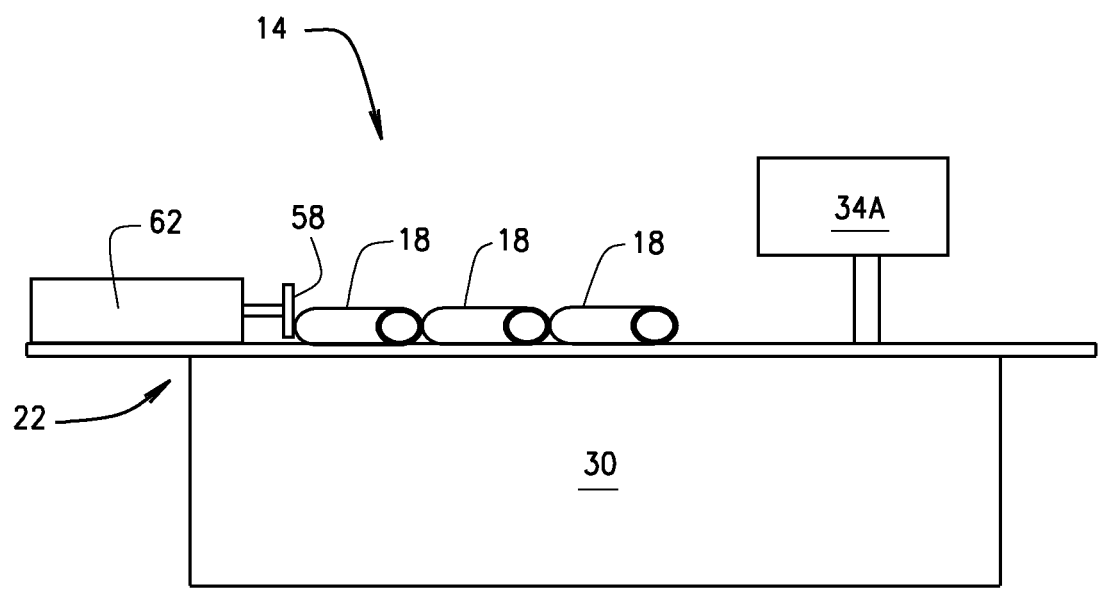
FIG. 4A is schematic of the X-ray computed tomography machine included in the system shown in FIG. 1 having the sample delivery platform comprising a push rod assembly, in accordance with various embodiments of the present disclosure.
Figure 4B:
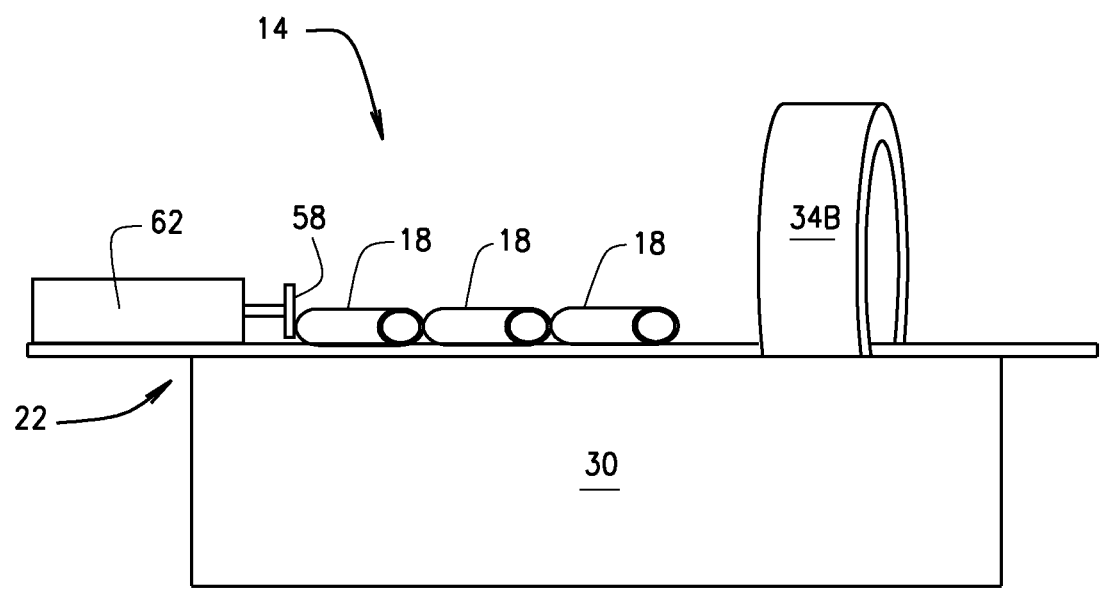
FIG. 4B is schematic of the X-ray computed tomography machine included in the system shown in FIG. 1 having the sample delivery or support platform comprising a push rod assembly, in accordance with various other embodiments of the present disclosure.

Referring now to FIGS. 4A and 4B, in various other embodiments, it is envisioned that the sample delivery/support platform 22 can comprise a push rod assembly mounted to the base cabinet 30 of the X-ray scanner system 14. The push rod assembly generally comprises a push rod or piston rod 58 operably connected to a push rod actuator 62, e.g., a hydraulic or pneumatic actuator. The push rod actuator 62 is operable to extend and retract the push rod 58 longitudinally over a sample platform 66 mounted to the base cabinet 30. More specifically, the sample(s), or sample container(s) 18 having the respective seed cotton sample disposed therein, can be placed on the sample platform 66, whereafter the push rod actuator 62 can be actuated to extend the push rod 58 longitudinally along the top surface of the sample platform 66. Consequently, the push rod 58 will push the sample(s) or sample container(s) 18 along the top surface of the sample platform 66 to thereby position each seed cotton sample, or sample container 18 and respective seed cotton sample, within the imaging field for a predetermined amount of time, or convey each sample or sample container through the imaging field of the image data generation assembly 34 such that image data of each respective seed cotton sample can be captured.

Figure 5A:
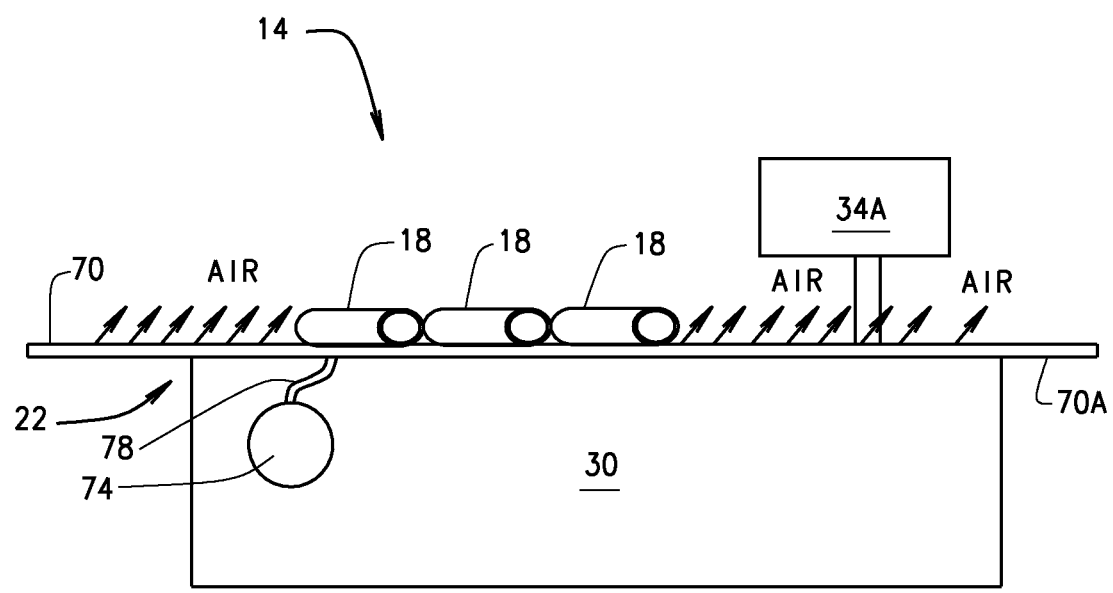
FIG. 5A is schematic of the X-ray computed tomography machine included in the system shown in FIG. 1 having the sample delivery or support platform comprising an air track assembly, in accordance with various embodiments of the present disclosure.
Figure 5B:
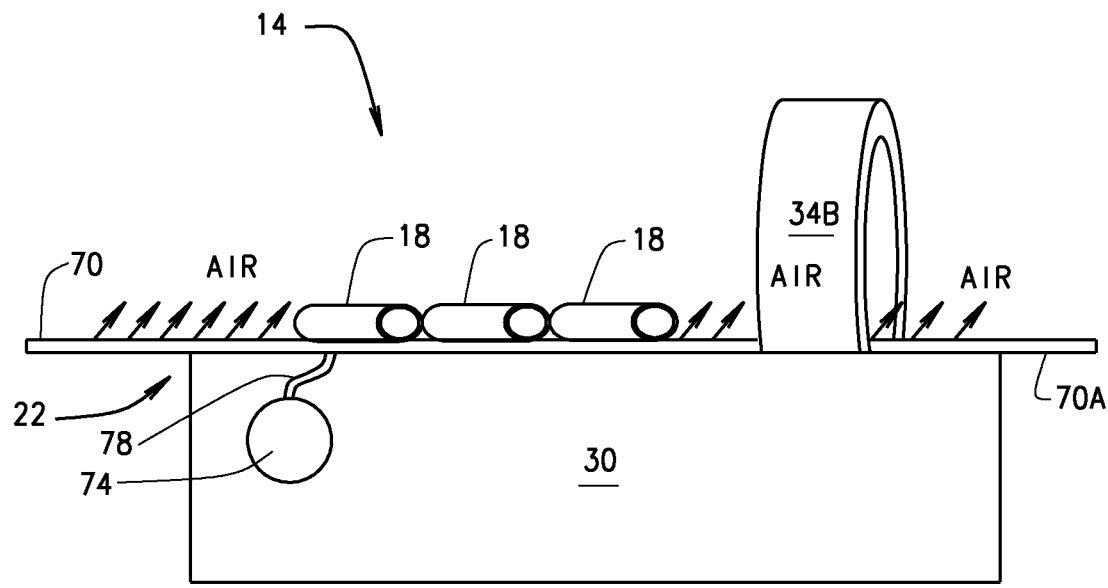
FIG. 5B is schematic of the X-ray computed tomography machine included in the system shown in FIG. 1 having the sample delivery or support platform comprising an air track assembly, in accordance with various embodiments of the present disclosure.

Referring now to FIGS. 5A and 5B, in various other embodiments, it is envisioned that the sample delivery/support platform 22 can comprise an air track assembly mounted to the base cabinet 30 of the X-ray scanner system 14. The air track assembly generally comprises an air track 70 and an air compressor/generator 74 fluidly connected to the air track 70 via an air hose 78. The air compressor 74 is operable to generate compressed air and provide the compressed air to the air 70 at a desired pressure, e.g., 10-150 psi, via the air hose 78. The air track 70 comprises a plurality of air orifices through which the compressed air passes to generate a plurality of air jets. The air orifices are angled (at any desired angle) such that the air jets are angled toward a distal end 70A of the air track 70 such that air jets will lightly lift an object placed on the air track 70 off the air track and convey the object along the length of the air track 70 toward the distal end 70A. Such an object can be stopped and placed anywhere along the air track simply by reducing or ceasing the flow of air from the air compressor 74. More specifically, the sample(s), or sample container(s) 18 having the respective seed cotton sample disposed therein, can be placed on the air track 70, whereafter the air compressor 74 can be activated to generate the air jets flowing from the air orifices. Air coming out of the air jets will then controllably move the sample(s) or sample container(s) 18 along the air track 70 toward the distal end 70A. Consequently, via the air jets, the sample(s) or sample container(s) will be conveyed along air track 70 to position each seed cotton sample, or sample container 18 and respective seed cotton sample, within the imaging field for a predetermined amount of time, or convey each sample or sample container through the imaging field of the image data generation assembly 34 such that image data of each respective seed cotton sample can be captured.

Although the X-ray scanner system 14 is exemplarily illustrated in a horizontal configuration throughout the various figures, it is envisioned that the X-ray scanner system can also be configured in a vertical orientation, and remain within the scope of the present disclosure. In such vertical embodiments the sample delivery/support platform 22 can comprise a gravitational sample delivery/support platform that utilized the force of gravity to position each sample, or sample container 18 and respective seed cotton sample, within the imaging field for a predetermined amount of time, or convey each respective seed cotton sample through the imaging field of the image data generation assembly 34 such that image data of each respective seed cotton sample can be captured.

In various embodiments, it is envisioned that the samples can be placed on a stationary sample delivery/support platform 22 (i.e, the sample delivery/support platform 22 is stationary) and the image data generation assembly 34 can move relative to the samples, e.g. using tracks or robotics in the lab or by a mobile platform in a field. In such embodiments, the samples are disposed on the stationary sample delivery/support platform 22 such that the stationary sample delivery/support platform 22 delivers, e.g., provides, the samples to the movable image data generation assembly 34, whereby the movable image data generation assembly 34 moves over the stationary samples to capture the image data.

It is further envisioned, that in various embodiments, the sample delivery/support platform 22 can the field or plot in which the samples are growing, or still connected to the respective plants. In such embodiments, the analysis system 10 can comprise a mobile system, wherein the X-ray scanner system 14 is disposed on a mobile platform or vehicle. In such embodiments, the system 10, particularly the X-ray scanner system 14, can automatically or manually moved through the field (or to selected locations within the field) such that the samples, still connected to the respective plants, can be positioned within the imagine field of the image data generation assembly 34/34A. Thereafter, the image data of selected samples can be captured and analyzed as described herein. In various implementations, the mobile system 10 can be a stand-alone system configured solely to capture image data of selected samples and analyze the image data as described herein. Or, in various other implementations, the mobile system 10, particularly the image data generation assembly 34/34A, can be part of a more complex, multi-functional, automated 'Smart' system, such as the system described in PCT Application PCT/US2015/045301, titled Apparatus And Methods For In-Field Data Collection And Sampling, filed Aug. 14, 2015, and corresponding U.S. Provisional Application 62/037,968, filed Aug. 15, 2014, the disclosure of each being incorporated by reference herein in their entirety. Such a system would be useful in outdoor (e.g. an agricultural field) conditions and indoor (e.g. a laboratory, glass house, greenhouse, and/or growth chamber) conditions.

Furthermore, it is envisioned that the basic elements/component of the system 10 (e.g., the X-ray image data generation assembly 34/34A and the computer based data analysis system 26) and the image data collection and analysis processes described herein can be implemented utilizing any other feasible structure, system, apparatus, or mobile platform suitably structured and operable for presenting samples to the X-ray image data generation assembly 34/34A, whereby the image data can be captured and analyzed as described herein.

Figure 6:
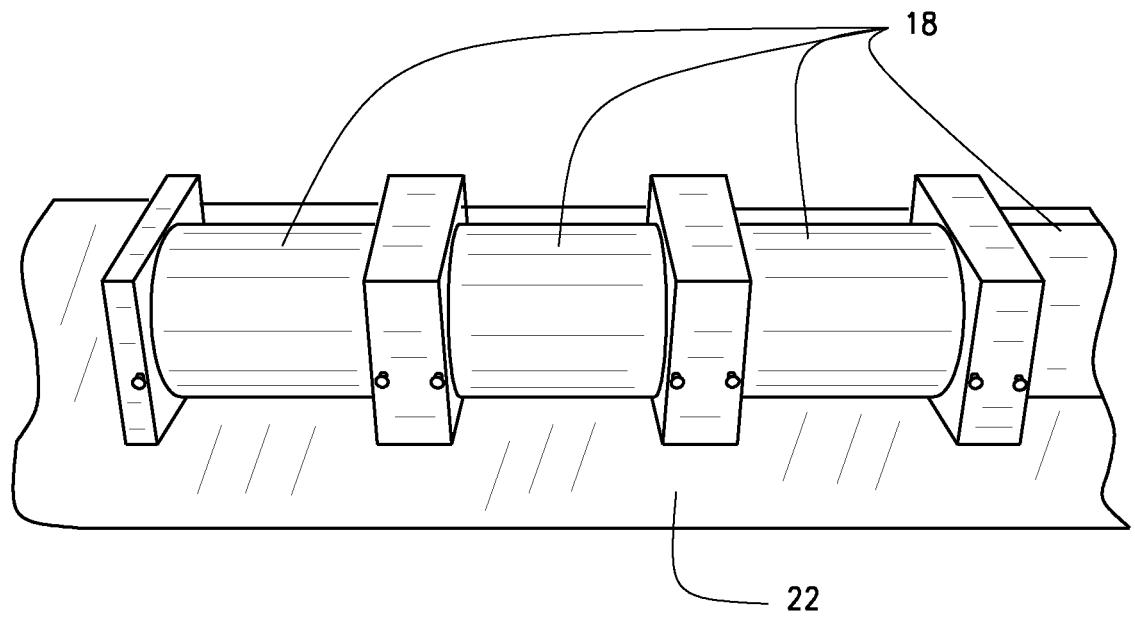
FIG. 6 is an isometric view of a linear array of seed cotton sample containers included in the system shown in FIG. 1, in accordance with various embodiments of the present disclosure.
Figure 7:
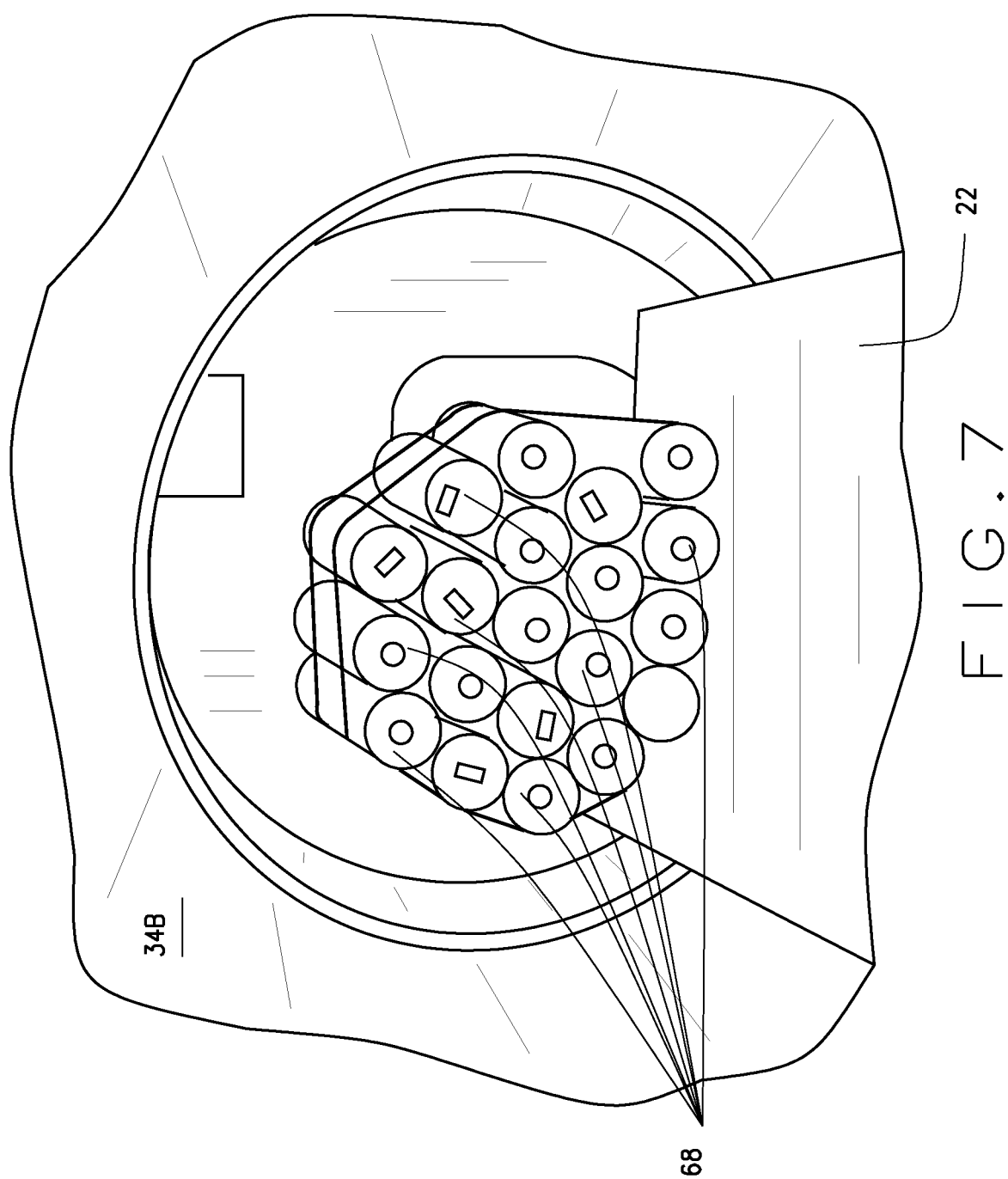
FIG. 7 is an isometric view of a stacked array of seed cotton sample containers included in the system shown in FIG. 1, in accordance with various embodiments of the present disclosure.

Referring now to FIGS. 6 and 7, as described above, in various embodiments, each seed cotton sample can be disposed within a respective sample container 18. In such embodiments each sample container 18 is structured to have a respective seed cotton sample disposed therein, each seed cotton sample comprising an amount of intact seed cotton grown from a particular type of seed, i.e., seed having particular genotype and/or phenotype characteristics or traits. Each sample container 18 can have any desired and suitable shape or size. For example, each sample container can be a hollow container having the shape of a cylindrical, cubical, polyhedronal, pyramidal, tetrahedonal, ellipsoidal, spherical, etc. For example, in various embodiments, as exemplarily illustrated in FIGS. 6 and 7, the sample containers 18 can be structured to have a cylindrical shape having a 4 inch diameter and being 1 foot in length. Alternatively, the sample container 18 can be a bag or envelope having no particular rigid shape. Additionally, the seed containers 18 can be constructed of any suitable material such that attenuation characteristics can be accounted for during the image analysis procedures, e.g., carbon or a suitable plastic or other polymer.

Furthermore, the plurality of sample containers 18 can be configured in any desired arrangement, array or matrix and positioned within the imaging field for a predetermined amount of time, or conveyed through the imaging field of the image data generation assembly 34 to capture the image data of each respective seed cotton sample. For example, it is envisioned that in various embodiments the sample containers 18 can be configured in a linear array, wherein the sample containers 18 are placed on the sample delivery/support platform 22 in an end-to-end arrangement, as exemplarily illustrated in FIG. 6. Alternatively, in various other embodiments wherein the image data generation assembly comprise CT scanner system 34B, it is envisioned that the sample containers 18 can be configured in a stacked array, wherein the sample containers 18 are arranged and retained side-by-side and stacked in a plurality of layers to form a bundle of sample containers 18 (i.e., a stacked array), as exemplarily illustrated in FIG. 7.

In various embodiments, the sample is not in a container when subjected to X-Ray analysis. In various embodiments, the sample remains attached to the plant. In various embodiments, the sample is not harvested from the plant and/or is not harvested from the field and/or from the location where the plant is growing. In various embodiments, the sample is subjected to X-Ray analysis while still growing from a plant in a field, greenhouse, growth room, incubator, or other area suitable for growing plants.

Figure 8:
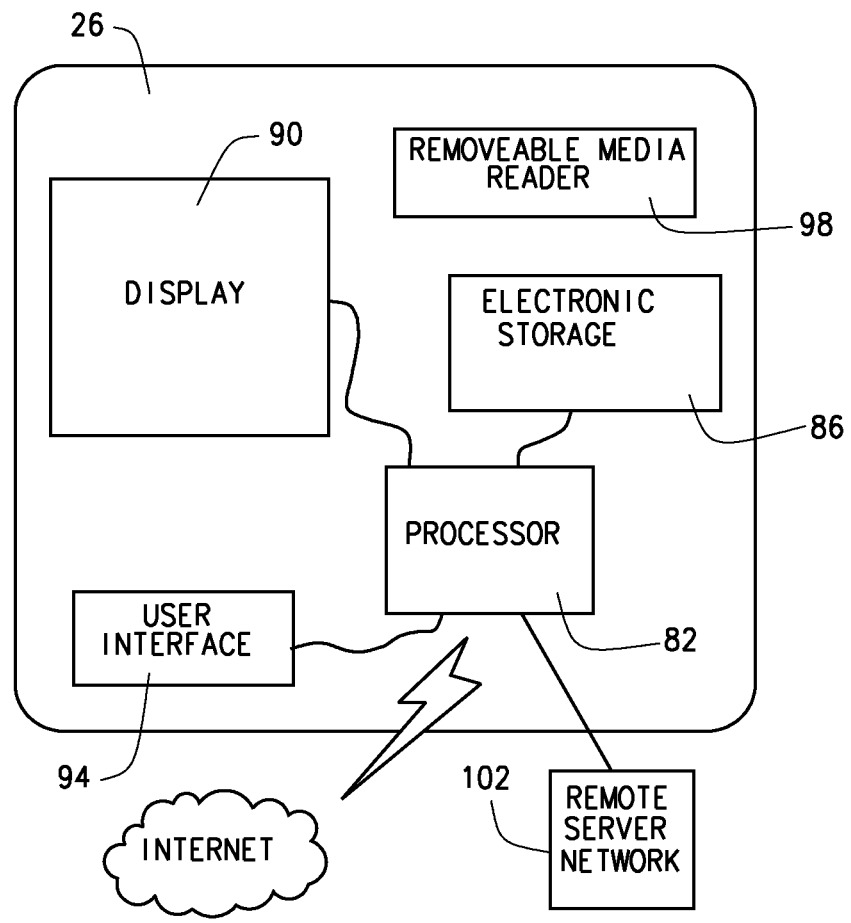
FIG. 8 is a block diagram of a computer based data analysis system of the system shown in FIG. 1, in accordance with various embodiments of the present disclosure.

Referring now to FIG. 8, in various embodiments, the computer based analysis system 26 is a computer based system that generally includes at least one processor 82 suitable to execute all software, programs, algorithms, described herein, e.g., the image analysis software, to analyze the image data captured by the X-ray scanner system 14 and generate the desired seed cotton sample metrics. The data analysis system 26 can additionally include at least one electronic storage device 86 that comprises a computer readable medium, such as a hard drive or any other electronic data storage device for storing such things as software packages or programs and algorithms (e.g., the image analysis software), and for storing such other things as digital information, data, look-up tables, spreadsheets and databases. Furthermore, the data analysis system 26 can include a display 90 for displaying such things as information, data and/or graphical representations, and at least one user interface device 94, such as a keyboard, mouse, stylus, and/or an interactive touch-screen on the display 90. In various embodiments the data analysis system 26 can further include a removable media reader 98 for reading information and data from and/or writing information and data to removable electronic storage media such as floppy disks, compact disks, DVD disks, zip disks, flash drives or any other computer readable removable and portable electronic storage media. In various embodiments the removable media reader 98 can be an I/O port utilized to read external or peripheral memory devices such as flash drives or external hard drives.

In various embodiments, the data analysis system 26, i.e., the processor 82 can be communicatively connectable to a remote server network 102, e.g., a local area network (LAN), via a wired or wireless link. Accordingly, the data analysis system 26 can communicate with the remote server network 102 to upload and/or download data, information, algorithms, software programs, and/or receive operational commands. Additionally, in various embodiments, the data analysis system 26 can be structured and operable to access the Internet to upload and/or download data, information, algorithms, software programs, etc., to and from internet sites and network servers.

Figure 9C:
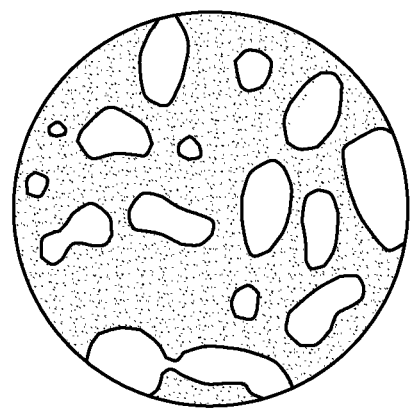
FIG. 9C is an exemplary illustration of the 3D computed tomography image data shown in FIG. 9A after processing by the image analysis software, showing the amount of lint in the section of seed cotton shown in FIG. 9A, in accordance with various embodiments of the present disclosure.
Figure 9B:
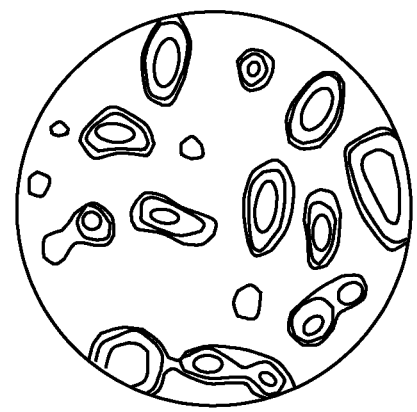
FIG. 9B is an exemplary illustration of the 3D computed tomography image data shown in FIG. 9A after processing by image analysis software, showing the number, size and amount of seed in the section of seed cotton shown in FIG. 9A, in accordance with various embodiments of the present disclosure.
Figure 9A:
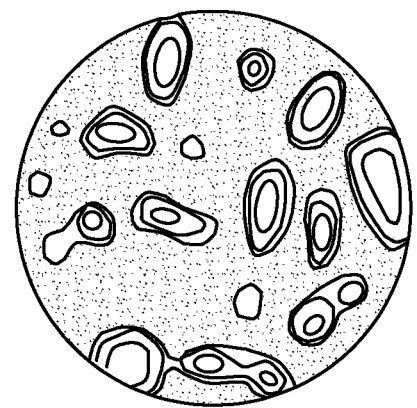
FIG. 9A is an exemplary illustration of a 3D computed tomography image data of a section of seed cotton disposed within one of the sample containers similar to those shown in at least FIGS. 1B, 2B, 3A, 4A, 4B, 5A, 5B, 6 and 7 using the X-ray computed tomography machine shown at least in FIGS. 1B, 2B, 3B, 4B and 5B, in accordance with various embodiments of the present disclosure.
Figure 9G:
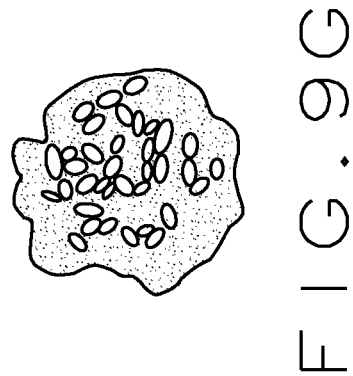
FIG. 9G is an exemplary illustration of the 2D X-ray image data shown in FIG. 9E after processing by image analysis software, showing the number, size and amount of seed in the section of seed cotton shown in FIG. 9E, in accordance with various embodiments of the present disclosure.
Figure 9F:
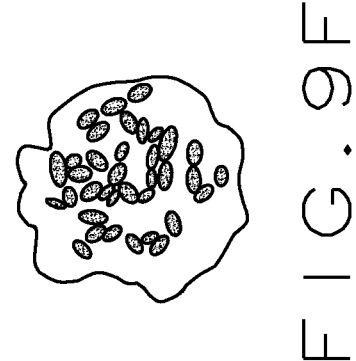
FIG. 9F is an exemplary illustration of the X-ray image data shown in FIG. 9E after processing by the image analysis software, showing the amount of lint in the section of seed cotton shown in FIG. 9E, in accordance with various embodiments of the present disclosure.
Figure 9E:
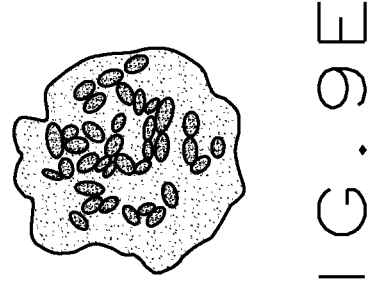
FIG. 9E is an exemplary illustration of a 2D X-ray image data of a section of seed cotton sample similar to those shown at least in FIGS. 1A, 2A and 3B using the 2D X-ray machine shown at least in FIGS. 1A, 2A, 3A, 4A and 5A, in accordance with various embodiments of the present disclosure.

Referring now to FIGS. 9A, 9B, 9C, 9E, 9F and 9G, as described above, the seed cotton analysis system 10 is operable to have an intact cotton sample, or sample container 18 having an intact cotton sample therein, in the imagine field of the image data generation assembly 34 (e.g., 34A or 34B), (as described herein, in various embodiments each respective sample conveyed into the imaging field), whereafter the image data generation assembly 34 (e.g., 34A or 34B) generates the plurality X-ray signals (i.e., the imaging field) that are attenuated by the respective seed cotton sample positioned within the imaging field. FIG. 9A is an exemplarily illustration of the 3D attenuated signals, i.e., a virtual 'slice', of specific area of an intact cotton sample disposed within a sample container 18 captured by the CT image data generation assembly 34B, while FIG. 9E is an exemplarily illustration of the 2D attenuated signals of specific area of an intact cotton sample disposed captured by the X-ray image data generation assembly 34A. Subsequently, the captured attenuated signals are compiled and processed (in CT embodiments tomographically processed) to generate the respective 2D or 3D image data, whereafter the 2D or 3D image data is processed, via the image analysis software, to determine the desired metric(s) of each of the intact cotton samples. For example, the attenuated signals can be processed and analyzed to determine a percentage of cotton lint in each of the seed cotton samples. More particularly, when a seed cotton sample of the appropriate size is analyzed utilizing the system 10, there is a statistical relationship between X-ray attenuation of the lint and seed in the sample and the respective amount of lint and seed by weight in the sample. The image analysis software is executed to process the image data captured by the image data generation assembly 34 to determine a lint percent (LP) of each respective sample.

Empirical data has shown that compaction of the samples, e.g., compaction within the sample containers 18, can skew the statistical relationship between X-ray attenuation of the lint and seed in the sample and the respective amount of lint and seed by weight in the sample. Hence, the amount of sample compaction can be a factor used to calibrate the results yielded via execution of the image analysis software.

Execution of the image analysis software will analyze the attenuated signals (i.e., the image data captured shown in FIGS. 9A and 9E) using segmentation procedures to filter and partition the attenuated signals into attenuated signals that represent the seed in the respective sample, as exemplarily illustrated in FIGS. 9B and 9F, and into attenuated signals that represent the lint in the respective sample, as exemplarily illustrated in FIGS. 9C and 9G. Then, based on the partitioned signals, the image analysis software determines a lint percent (LP) of each respective sample. For example, in various embodiments, execution of the image analysis software will analyze the attenuated signals (shown in FIGS. 9A and 9E) and determine which attenuated signals are above given threshold. Signals above the threshold (shown in FIGS. 9B and 9F) are identified seeds or trash. Conversely, attenuated signals below the given threshold (shown in FIGS. 9C and 9G) are identified as lint. The LP is then simply calculated as lint attenuation (FIGS. 9C and 9G) divided by the total attenuation (FIGS. 9A and 9F), i.e., the attenuation identified as seed plus the attenuation identified as seed and trash. In various implementations, the image analysis software can utilize a calibration curve to estimate the weight of the lint versus the weight of the seed and trash in the respective sample. In various embodiments, one or more attenuation thresholds can be implemented to distinguish between seed, trash and lint. Hence, the individual amounts of seed and trash can be determined to further improve the accuracy of the LP determination.

Referring now to FIG. 9D, determination and selection of the attenuation threshold is an important component in the analysis of the attenuated signals, as described herein, as the accuracy of the results will be predicated on the value of the threshold. That is, the attenuation threshold must be calculated or determined such that attenuation of signals above the threshold accurately identifies seed or trash, and attenuation signals below the threshold accurately identify lint. It is envisioned that various methods of determining the optimal threshold (i.e., the threshold value that will yield the most accurate LP data) can be implemented and remain within the scope of the present disclosure. For example, as illustrated in FIG. 9D, in various implementations, the threshold was empirically determined, via image analysis, to be between 200 and 400, e.g., 300. It is further envisioned that environmental conditions, e.g., environmental temperature and/or humidity, and/or moisture and/or compaction of the samples during analysis, can be considered when determining the optimal attenuation threshold value.

In various implementations, the image analysis software can be executable to further partition the attenuation signals to determine other metrics of each sample. For example, the attenuation signals can be further processed and analyzed to determine an amount of trash, e.g., plant stems, leaves and other foreign material, in each respective sample, thereby increasing the accuracy of the LP generated.

It is also envisioned the seed cotton samples can be stored in a cassette-based storage and retrieval system that is operably to, via automation, retrieve any number of sample containers 18 having desired seed cotton sample(s) disposed therein, and place the selected sample containers 18 on the sample delivery/support platform 22. Then, once each respective seed cotton sample is conveyed to the imaging field of the image data generation assembly 34 and scanned, as described above, the sample containers are automatically evacuated and placed in a bulk collection bin, or back in the cassette-based storage.

It is also envisioned that, based on the particular seed cotton metrics determined, e.g., a seed density of each sample; a seed maturity of each sample; a seed viability of each sample; a seed oil content of each sample, etc., execution of the image analysis software can further include algorithms to determine various lint and/or seed treatment choices that can be made. For example, such algorithms can be executed to utilize the determined metrics to making decisions about a treatment for each seed cotton sample, e.g. keep or discard, or apply the selected treatment. It is further envisioned that the system 10 can be implemented as part of a larger mobile analysis and treatment platform that can be driven through a field, analyze the seed cotton, as described herein, and apply any desired treatment based on the analysis. It is still further envisioned that the system 10 and the image analysis methods described herein can be automated and the image data provided in real time to a server that a remote operator, e.g., a breeder, can access remotely. Thus, raw or annotated data could be provided to such an operator monitoring the processes from an office console, along with a recommended treatment. The operator could then issue commands to the mobile analysis and treatment platform to apply the treatment desired by the operator to the scanned and analyzed seed cotton sample.

EXPERIMENTS

Experiments were performed utilizing the seed cotton analysis system 10 to test the accuracy, consistency and reliability of the seed cotton analysis system 10 and methods described above The experiments and results are described below

Experiment 1

The experiment set up includes selecting 40 different genotypes of seed cotton samples. Each seed cotton sample comprised approximately 150 grams of seed cotton. Each sample was conditioned in climate cabinet set at 40% relative humidity and 71.5° F. for one week. Each sample was then weighed and immediately sealed in a respective zip-lock bag. Each sample was then transferred to a respective sample container 18 comprising a cylindrical carbon tube having 3 inch diameter and being 1 foot in length. Each sample was then analyzed using the seed cotton analysis system 10, as described above, wherein the image data generation assembly comprised a CT scanner set at 100 kV, 150 mAs, 0.35 pitch, 0.5 s rotation speed, 600 micron slices, and 102 display field of view (DFOV).

After each sample was scanned and analyzed using the seed cotton analysis system 10, each sample was then mechanically ginned using a 10-saw gin to separate lint, seed, and trash components. The trash was separated from the seed. The separated lint, seed and trash components for each sample was then conditioned in climate cabinet set at 40% relative humidity and 71.5° F. for one week. Thereafter, the lint, seed and trash components for each sample was weighed and immediately sealed in zip-lock bags. The separated lint and seed for each sample was then transferred to a respective sample container 18 comprising a cylindrical carbon tube having 3 inch diameter and being 1 foot in length. Each sample was then analyzed using the seed cotton analysis system 10 to obtain total attenuation for the separated lint, seed and trash components, as described above, wherein the image data generation assembly comprised a CT scanner set at 100 kV, 150 mAs, 0.35 pitch, 0.5 s rotation speed, 600 micron slices, and 102 DFOV.

Experimental Results

Figure 10:
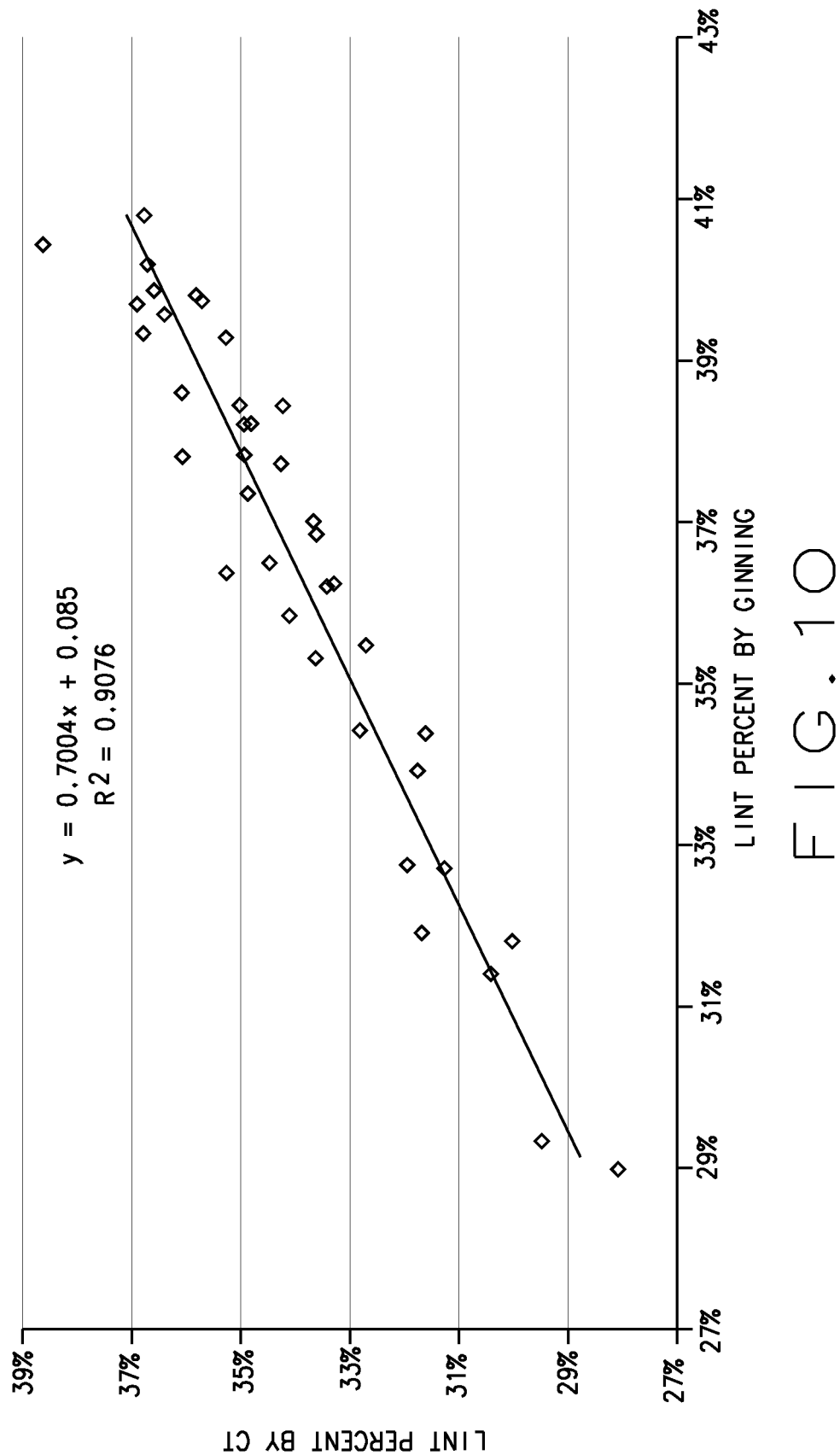
FIG. 10 is a graph illustrating the lint percent (LP) determined by scanning and processing 40 seed cotton samples using the seed cotton analysis system shown in FIG. 1, versus the LP determined by ginning, in accordance with various embodiments of the present disclosure.

FIG. 10 is a graph illustrating the lint percent (LP) determined by scanning and processing the 40 intact cotton samples using the seed cotton analysis system 10 and corresponding image analysis software prior to ginning the samples (illustrated as LP by CT), versus the LP determined by ginning.

Figure 11:
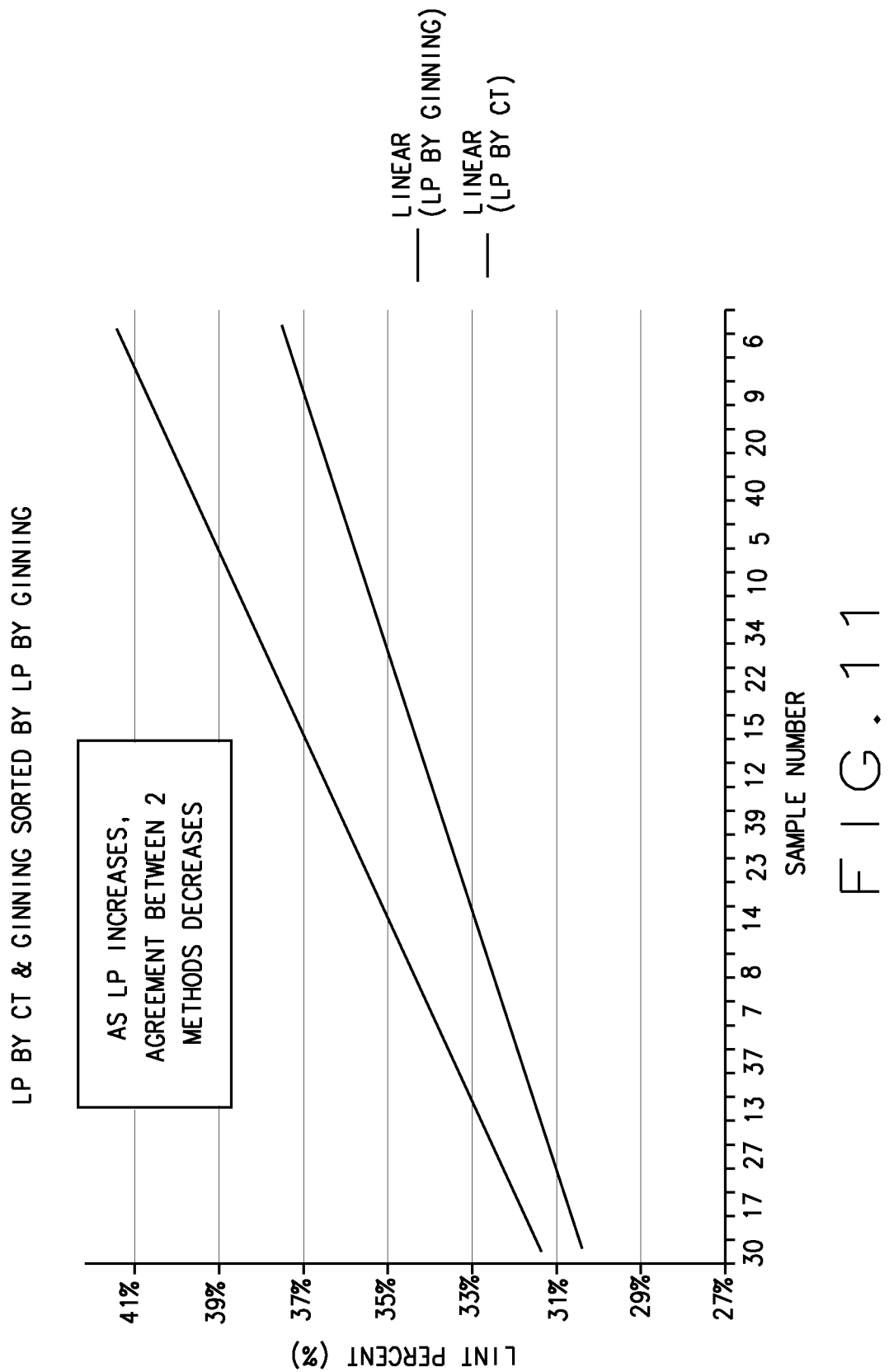
FIG. 11 is a graph of ling percent versus sample number illustrating the difference in the trends of LP determined by ginning and by computed tomography when the samples are sorted by the LP determined by ginning, in accordance with various embodiments of the present disclosure.

FIG. 11 is a graph of lint percent versus sample number illustrating the difference in the trends of LP determined by ginning (illustrated as LP by Ginning) and by CT (illustrated as LP by CT) when samples are sorted by LP by Ginning. The difference observed between the LP Ginning and the LP by CT demonstrate the systematic errors introduced by the selection of a single segmentation level (threshold=300) which is used during the CT image analysis as well as systematic errors during the ginning process which include seeds and trash remained in post-gin lint component, lint remained in post-gin seed component, lint remained in post-gin trash component. One threshold level introduces a slight over or under-estimation of the true total attenuation for the lint, seed, or trash components, similar to that depicted in FIG. 9D.

Figure 12:
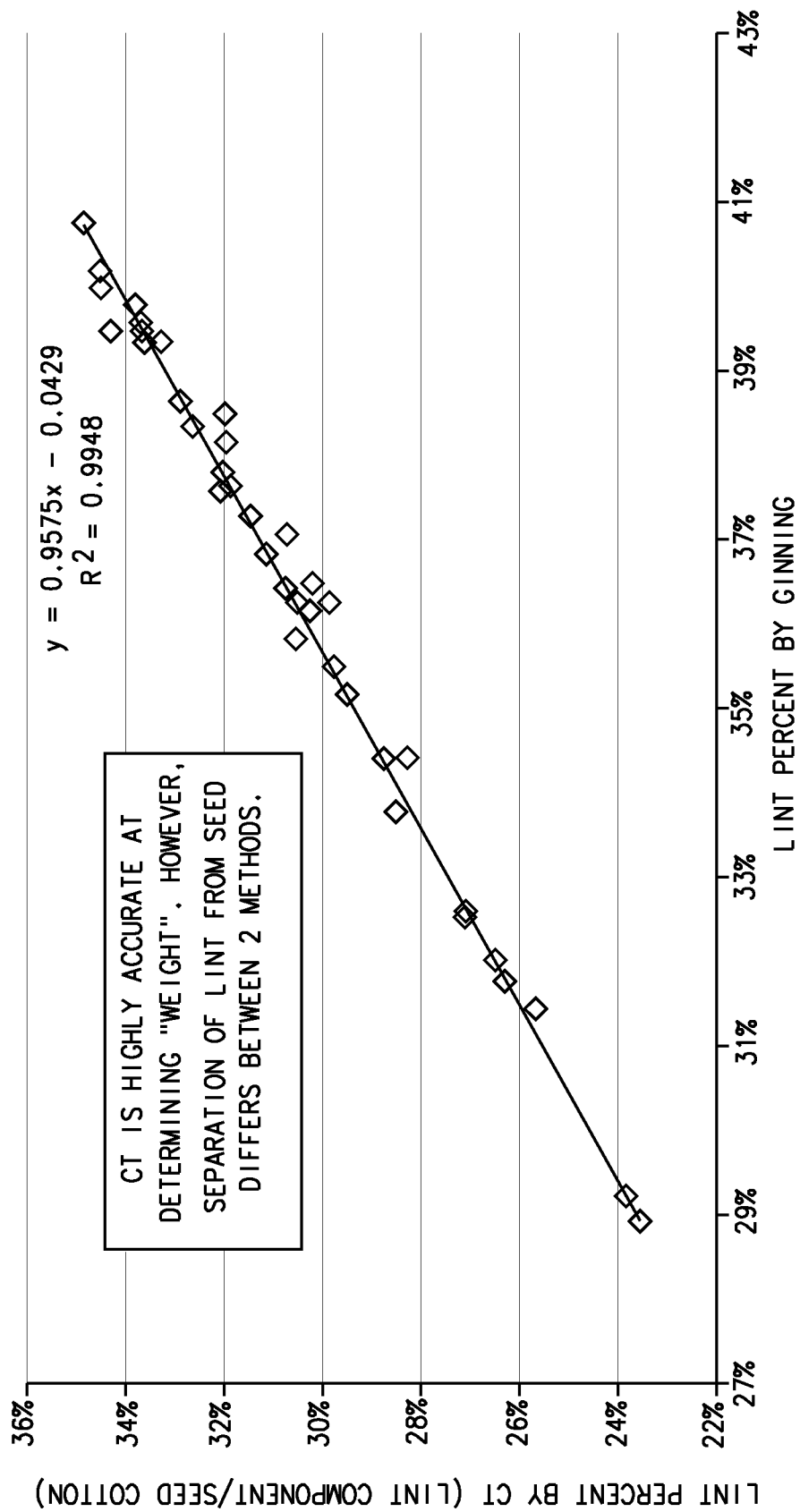
FIG. 12 is a graph comparing the LP determined by computed tomography where the attenuation of the lint component after ginning is divided by the seed cotton attenuation before ginning versus the LP determined by ginning, in accordance with various embodiments of the present disclosure, in accordance with various embodiments of the present disclosure.

FIG. 12 is a graph comparing the LP determined by CT where the attenuation of the lint component after ginning is divided by the seed cotton attenuation before ginning versus the LP determined by ginning, in accordance with various embodiments of the present disclosure, in accordance with various embodiments of the present disclosure. This provides evidence that the difference between trend lines observed in FIG. 11 is due to differences in how the components are separated in each of the methodologies.

Figure 13:
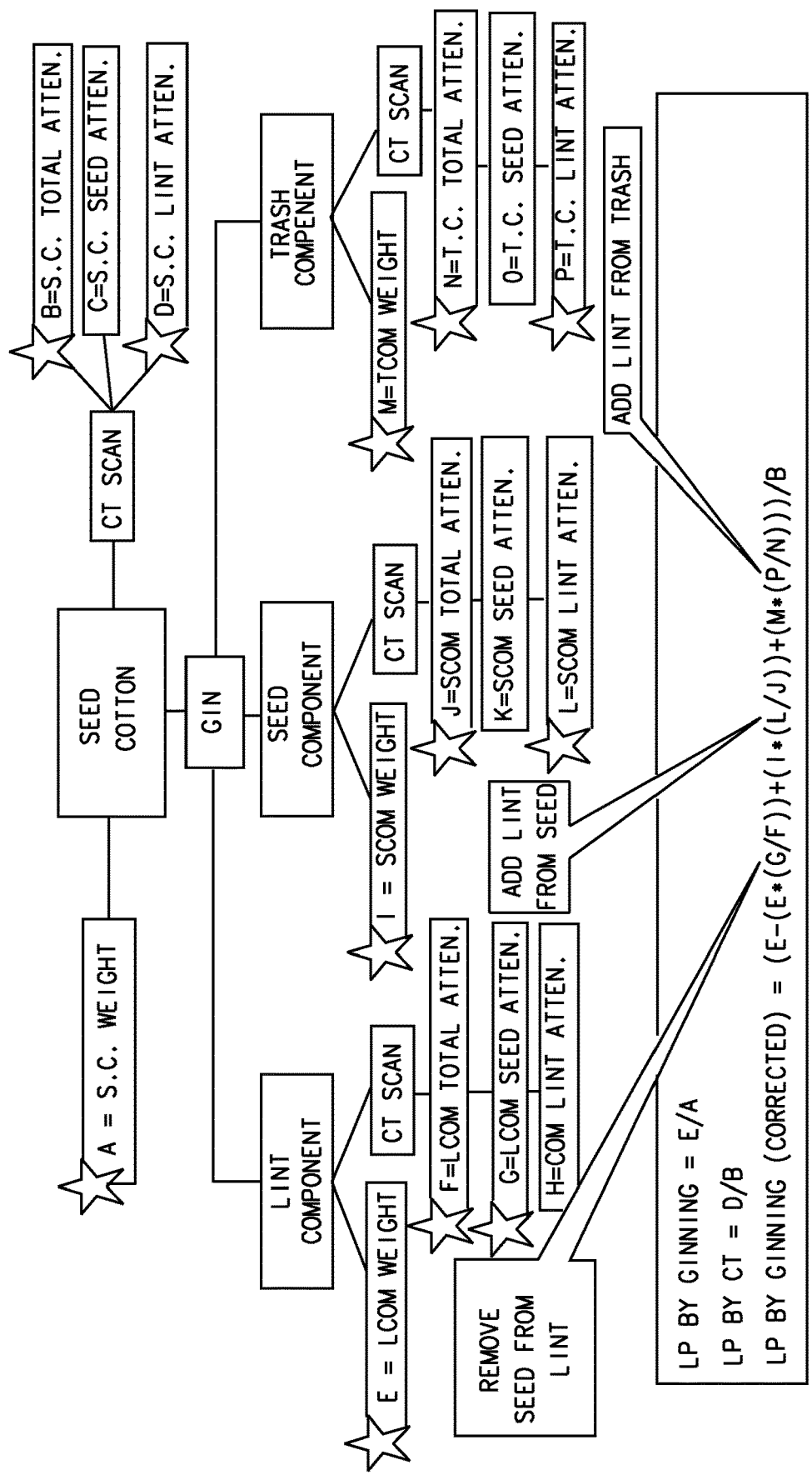
FIG. 13 is a diagram illustrating a exemplary correction process or algorithm executed on the results shown in FIG. 10, in accordance with various embodiments of the present disclosure.

FIG. 13 is a diagram illustrating a correction process or algorithm executed on the results shown in FIG. 10. CT scans were conducted on the intact cotton samples and again on the lint, seed, and trash components after ginning. The same thresholds were applied to the component scans as was to the intact seed cotton scan enabling the identification of seed and trash remained in the lint component, lint remained in the seed component, and lint remained in the trash component. The correction process utilized the component scans to account for errors due to ginning, e.g., seeds remained in post-gin lint component, plus lint remained in post-gin seed component, plus lint remained in post-gin trash component. Both the CT and the ginning methodologies have systematic errors. However, it is believed that inherent errors in the ginning process tend to be more variable and less predictable than those in the CT methodology. Thus, the correction factors were applied to the ginning process to stabilize the noise in order due to ginning and not to genotype nor environmental conditions in which the genotype was grown to provide a more realistic evaluation of the CT methodology.

Figure 14:
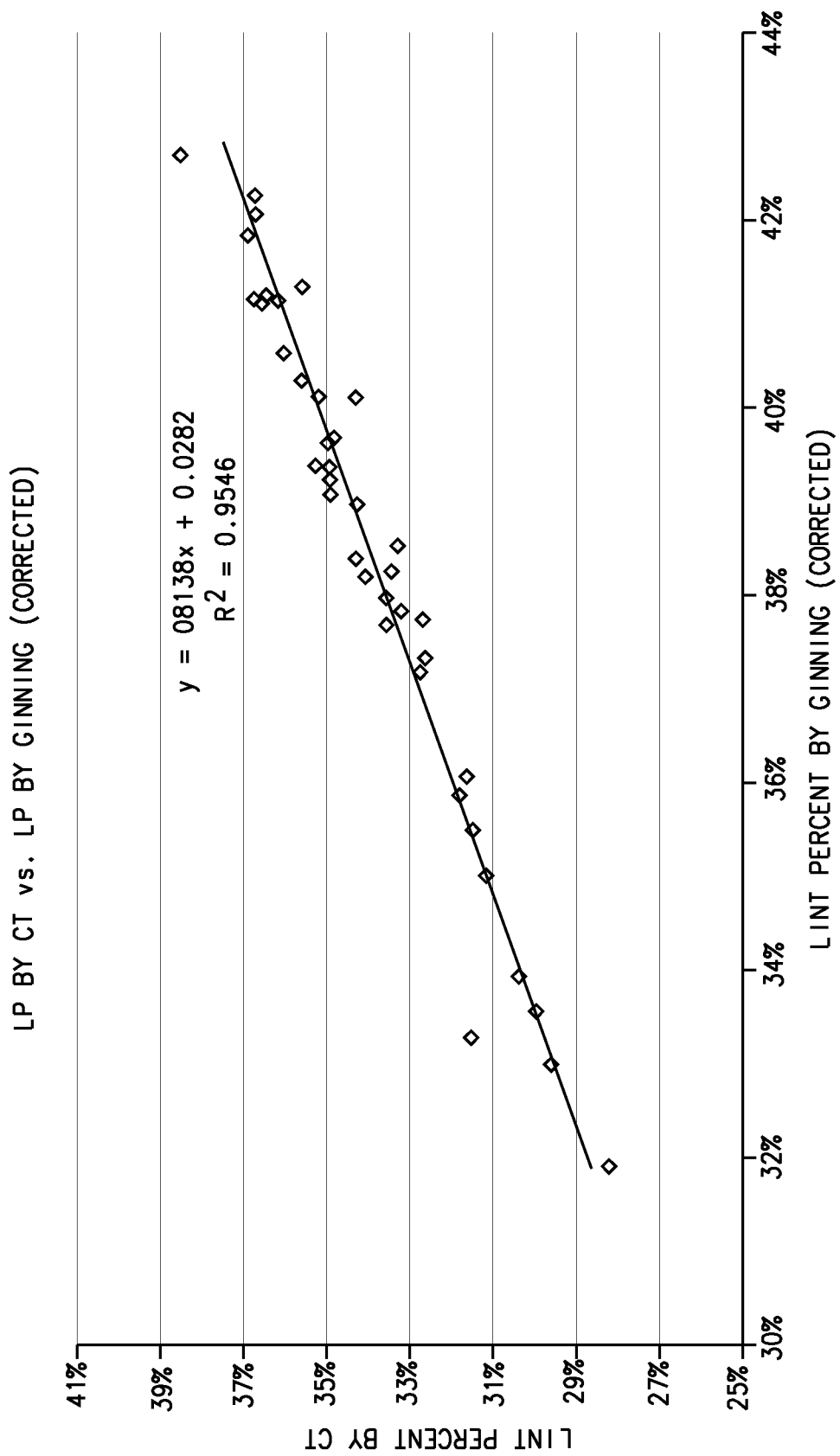
FIG. 14 is a graph illustrating the results shown in FIG. 10 corrected by the process/algorithm shown in FIG. 13, in accordance with various embodiments of the present disclosure.
Figure 15:
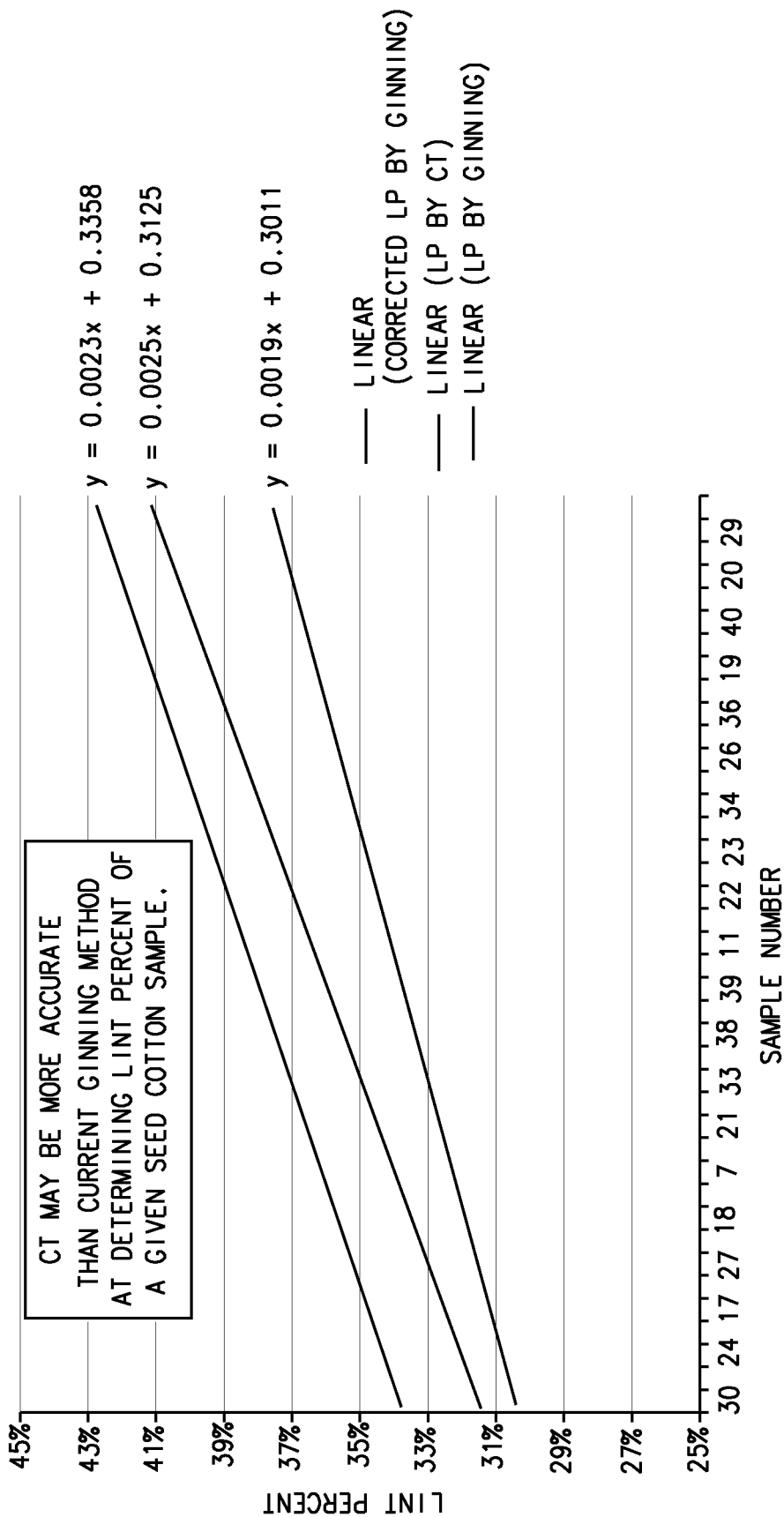
FIG. 15 is a graph illustrating the LP determined by ginning (as shown in FIG. 10) before and after application of a correction factor, in accordance with various embodiments of the present disclosure.

FIG. 14 is a graph illustrating the results shown in FIG. 10 corrected by the process/algorithm shown in FIG. 13. Note the improved correlation (R2=0.95) compared to the uncorrected results shown in FIG. 10. FIGS. 15 and 16 are graphs illustrating the lint percent (LP) determined after the samples had been ginned (as shown in FIG. 10) before and after application of the correction factor. The correction factor strengthens the correlation between the CT and ginning LP results, i.e., it brings the first and third trend lines in FIG. 15 closer together to generate the second trend line with a similar slope. Since the offset between the first and second trend lines is known to be caused by the selection of a single threshold value during image analysis, it can be corrected using a simple correction factor to essentially superimpose these two curves. Similarly, the correction improves the correlation between the CT versus ginning results for the low and high LP samples as demonstrated by the change in the "Before" and "After" correlation curves in FIG. 16. Note these corrections are not possible on samples that were not ginned. Hence, the three components (seed, lint, trash) image analysis approach becomes important because it provides the ability to make the corrections, e.g., for the trash component, without ginning.

Seed Cotton Metrics Results

The image analysis software was further executed to determine various seed cotton metrics.

FIG. 17 provides a comparison and contrast of different methods for determining seed metrics. ETOH is a method for measuring seed volume by measuring the displaced volume of ethanol caused by submerging a sample of seed(s). WinSEEDLE™ is a proprietary system where seeds are scanned on a two-dimensional optical scanner, and the images subsequently analyzed to calculate seed metrics. As is evident, the X-ray methodology enables the measurement of the widest range of seed metrics and at a superior throughput when compared to current seed metric methodologies.

FIG. 18 is a graphical illustration showing the number of seeds determined to be in each of the 40 samples (i.e., seed count) utilizing the system 10 versus a manual count of seeds from each respective sample after the samples had been ginned (i.e., manual fuzzy seed count), and versus a manual count of seeds from each respective sample after the seeds had been delinted (i.e., delinted seed count).

FIG. 19 provides graphical illustrations of average seed volume by CT versus ETOH displacement, and versus WinSEEDLE™ analysis.

FIG. 20 provides a histogram of seed volume. Particularly, FIG. 20 illustrates individual seed volume distribution for two different types of seed cotton samples determined by X-ray. This highlights the value of being able to measure seed metrics on an individual seed basis. Seed size has an indirect relationship to lint yield but a direct relationship to seed germination and seedling vigor. Thus, the ability to select genotypes which has a consistently large enough seed phenotype may enable breeders to simultaneously select for improved genetic potential for lint yield, seed germination and seedling vigor.

FIG. 21 is a graph illustrating the total seed surface area by CT (not filled) versus total seed surface area by WinSEEDLE™.

As a result of the experiment described above, it is envisioned that the seed cotton analysis system 10 and corresponding image analysis software can be utilized to determine many different seed cotton metrics, such as lint weight per unit seed surface area, number of lint fibers per unit seed surface area, the number of seeds in each sample, a seed density of each sample, a seed maturity of each sample, a seed viability of each sample, a seed oil content of each sample, a seed volume of each sample, the size, shape and/or surface area of seed in each sample, a lint density of each sample, the amount of trash (e.g., plant stems) in each sample, seed vigor, etc.

Experiment 2

This experiment tested the accuracy of the system 10 using the 2D X-ray image data generation assembly 34A (described above). The experiment set up includes preparing "Mock" seed cotton samples by weighing out the amounts, shown in Table 1 below, of lint and fuzzy seeds and mixing the two components to achieve reasonable distribution of the cotton seeds.

TABLE 1

| LINT WEIGHT (G) | SEED WEIGHT (G) | TOTAL WEIGHT (G) | SAMPLE NAME |
|---|---|---|---|
| 1.0470 | 3.2914 | 4.3384 | SPL 1 (24.1%) |
| 1.5320 | 3.5340 | 5.066 | SPL 2 (30.2%) |
| 2.0505 | 3.785 | 5.8355 | SPL 3 (35.1%) |

The round samples were prepared by compressing the samples by hand and positioning the sample within the imaging field of the image data generation assembly 34A, and the flat samples were prepared by squeezing round samples using a 2 mil sheet of Mylar and positioning the sample within the imaging field of the image data generation assembly 34A. Subsequently, 2D X-ray imaging was performed on each respective sample, as described above.

The following Table 2 sets forth various specific parameters of various samples tested for both round and flat samples.

TABLE 2

Parameter Optimization on Spl 3

| kV | Exposure (sec) | LP-round | LP-Flat |
|----|----------------|----------|---------|
| 15 | 20 | 27.3 | 29.3 |
| 20 | 20 | 43.8 | 42.3 |
| 25 | 6 | 34.7 | NC |
| 30 | 3.8 | 35.5 | NC |
| 35 | 2.8 | 25.5 | NC |

NC = data not collected

Seed Cotton Metrics Results

FIGS. 22A though 22F illustrate the resulting 2D X-ray image of a particular round seed cotton sample tested and a particular flat seed cotton sample tested. Particularly, FIGS. 22A and 22D show the non-attenuated image data for each respective sample, FIGS. 22B and 22E show the amount of lint of each sample derived by processing of the image data of FIGS. 22A and 22D by the image analysis software, and FIGS. 24C and 24F show the amount of seed in each sample derived by processing of the image data of FIGS. 22A and 22D by the image analysis software. As described above, the lint percent, and other seed metrics can be determined from the respective image data.

Additionally, the following Table 3 provides the actual lint percent (LP) versus the LP determined using the system 10 comprising the 2D X-ray data generation assembly 34A for 3 of the respective round samples and 3 of the respective flat samples.

TABLE 3

Lint Percent Calculations

| Sample | Total Spl Wt. | LP-Actual | LP-Round | LP-Flat |
|--------|---------------|-----------|----------|---------|
| 1 @ 25 kV | 4.34 | 24.1 | 19.9 | NC |
| 2 @ 25 kV | 5.07 | 30.2 | 30.6 | 27.3 |
| 3 @ 30 kV | 5.84 | 35.1 | 35.5 | 37.5 |

NC = data not collected

CONCLUSION

The above results show that the 2D X-ray technology can measure LP as indicated by LP-Round values in the second and third lines of the table above. These measures were obtained using optimal sample sizes, orientation, and acquisition parameters. The LP-Round value in the first line, and the LP-Flat values in the second and third lines do not provide accurate measures of LP due to one or more factors that are known to effect the x-ray measurement, e.g., inadequate sample size, inappropriate sample preparation and/or incorrect acquisition parameter selection.

In sum, the experiments described above show that LPs of any given seed cotton sample determined using the system 10 are very accurate and agree well with the LPs for the same samples determined by ginning the seed cotton which physically separates the lint from the seed to determine LP.

As described herein, it is envisioned that the X-ray scanner system 10 can exemplarily comprise 2D X-ray scanning or 3D CT scanning systems or machines to obtain the image data and subsequently process the image data using the image analysis software (as described above) and remain within the scope of the present disclosure.

It is further envisioned that determining seed cotton metrics, e.g., LP, utilizing the system 10 and image analysis software described above, will dramatically increase the speed and efficiency of determining such metrics over known methods, and do so in a very cost-effective manner.

It is further envisioned that the system 10 described above, and the implementation thereof, can be commercially employed as a pre-ginning systems and process to improve the separation of lint from seed during ginning of the seed cotton samples.

The description herein is merely exemplary in nature and, thus, variations that do not depart from the gist of that which is described are intended to be within the scope of the teachings. Such variations are not to be regarded as a departure from the spirit and scope of the teachings.

The invention claimed is:

1. A system for analyzing intact cotton, said system comprising:
a plurality of seed cotton sample containers, each seed cotton sample container structured and operable to retain an intact cotton sample;
a sample support platform structured and operable to have the intact cotton samples containers disposed thereon;
an X-ray scanner system including an X-ray image data generation assembly, the X-ray scanner system structured and operable to generate X-ray image data of one or more intact cotton sample retained within the one or more of the seed cotton sample containers disposed on the sample support platform within an imaging field of the X-ray image data generation assembly; and
a computer based system structured and operable to execute image analysis software to analyze the image data and determine at least one metric of each of the one or more intact cotton sample.

2. The system of claim 1, further comprising a sample support platform structured and operable to have the intact cotton samples disposed thereon within the imaging field.

3. The system of claim 2, wherein the sample support platform is further structured and operable to the move the intact cotton samples through the X-ray imaging field.

4. The system of claim 3, wherein the sample support platform comprises:
a bed; and
a linear stage structured and operable to linearly move at least a portion of the bed through the imaging field of the image data generation assembly.

5. The system of claim 3, wherein the sample support platform comprises a conveyor belt assembly, the conveyor belt assembly comprising a continuous conveyor belt and structured and operable to revolve the continuous conveyor belt through the imaging field of the image data generation assembly.

6. The system of claim 3, wherein the sample support platform comprises a push rod assembly, the push rod assembly system structured and operable to move the intact cotton samples through the imaging field of the image data generation assembly.

7. The system of claim 3, wherein the sample support platform comprises an air track assembly, the air track assembly structured and operable to move the samples through the imaging field the image data generation assembly.

8. A method for analyzing intact cotton, said method comprising:
   disposing one or more intact cotton samples within a plurality of seed cotton sample containers;
   disposing the plurality of seed cotton sample containers on sample support platform;
   presenting, via operation of the sample support platform, the plurality of seed cotton sample containers, thereby presenting the one or more intact cotton samples for imaging by an X-ray scanner system of a seed cotton analysis system;
   collecting X-ray image data for the one or more intact cotton sample, via the X-ray scanner system;
   analyzing the collected X-ray image data of the one or more intact cotton sample, via execution of image analysis software by a computer based system of the X-ray scanner system; and
   determining at least one metric of each of the at least one intact cotton sample.

9. The method of claim 8, wherein determining at least one metric of each of the at least one intact cotton sample comprises determining at least one of:
   lint percent of the intact cotton samples,
   number of seeds in the intact cotton samples,
   seed density of the intact cotton samples,
   number of lint fibers in the intact cotton samples,
   lint density of the intact cotton samples,
   mount of trash in the intact cotton samples,
   maturity level of seed in the intact cotton samples,
   viability of the seed in the intact cotton samples,
   oil content of the seed in the intact cotton samples,
   volume of seed in the intact cotton samples,
   size of the seed in the intact cotton samples,
   shape of the seed in the intact cotton samples,
   surface area of the seed in the intact cotton samples,
   disease quality of the seed in the intact cotton samples, and
   damage quality of the seed in the intact cotton samples.

10. The method of claim 9 further comprising at least one of:
   determining a moisture content of the at least one intact cotton sample and utilizing the determined moisture content as input data during the analysis of the collected image data for each intact cotton sample; and
   determining an amount of compaction of the at least one intact cotton sample; and utilizing the determined amount of compaction as input data during the analysis of the collected image data for the at least one intact cotton sample.

11. The method of claim 9, wherein the seed cotton analysis system additionally includes a sample support platform, and presenting the at least one intact cotton sample for imaging by the X-ray scanner system comprises one of:
   placing the at least one respective intact cotton sample on a bed of the sample support platform, and moving the at least one respective intact cotton sample through the imaging field, via a linear stage;
   placing the at least one respective intact cotton sample on a continuous conveyor belt of a conveyor belt assembly of the sample support platform, and revolving the continuous conveyor belt past image data generation assembly to move the at least one intact cotton sample through the imaging field;
   placing the at least one intact cotton sample on a table of the sample support platform, and pushing the at least one intact cotton sample through the imaging field, via a push rod assembly; and
   placing the at least one intact cotton sample on an air track of an air track assembly of the sample support platform, and moving the at least one intact cotton sample through the imaging field, via air jets of the air track assembly.

12. The method of claim 11 further comprising:
   disposing the at least one intact cotton sample within a respective one of a plurality of sample containers, and one of:
   disposing the respective sample containers on a sample support platform of seed cotton analysis system such that the sample containers are arranged in a single-file linear array; and
   disposing the respective sample containers on a sample support platform of seed cotton analysis system such that the sample containers are arranged in a stacked array.

13. The method of claim 9, wherein the seed cotton analysis system additionally includes a sample support platform, and wherein presenting the at least one intact cotton sample for imaging by the X-ray scanner system comprises one of:
   placing the at least one intact cotton sample on the sample support platform within an imaging field of an image data generation assembly of the X-ray scanner system; and
   placing the at least one intact cotton sample on the sample support platform and moving the image data generation assembly over the at least one intact cotton sample.

* * * * *